(12) United States Patent
Yoo

(10) Patent No.: US 8,969,070 B2
(45) Date of Patent: Mar. 3, 2015

(54) THIN-FILM LAYERED CENTRIFUGE DEVICE AND ANALYSIS METHOD USING THE SAME

(75) Inventor: Jae Chern Yoo, Pohang (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 394 days.

(21) Appl. No.: 12/863,684

(22) PCT Filed: Jan. 21, 2009

(86) PCT No.: PCT/KR2009/000306
§ 371 (c)(1),
(2), (4) Date: Jul. 20, 2010

(87) PCT Pub. No.: WO2009/093838
PCT Pub. Date: Jul. 30, 2009

(65) Prior Publication Data
US 2010/0297659 A1   Nov. 25, 2010

(30) Foreign Application Priority Data

Jan. 21, 2008   (KR) .................. 10-2008-0006890

(51) Int. Cl.
| | | |
|---|---|---|
| C12M 1/34 | (2006.01) | |
| C12M 3/00 | (2006.01) | |
| G01N 33/53 | (2006.01) | |
| G01N 35/00 | (2006.01) | |
| B01L 3/00 | (2006.01) | |

(52) U.S. Cl.
CPC ...... *G01N 33/5302* (2013.01); *G01N 35/00029* (2013.01); *G01N 35/00069* (2013.01); *B01L 3/502753* (2013.01); *G01N 2035/00247* (2013.01); *G01N 2035/00495* (2013.01)
USPC ....... 435/287.2; 435/288.5; 422/64; 422/68.1

(58) Field of Classification Search
None
See application file for complete search history.

(56) References Cited

U.S. PATENT DOCUMENTS

| | | | | |
|---|---|---|---|---|
| 6,302,134 | B1 * | 10/2001 | Kellogg et al. | 137/74 |
| 8,097,450 | B2 * | 1/2012 | Yoo | 435/288.5 |
| 2003/0054376 | A1 * | 3/2003 | Mullis et al. | 435/6 |
| 2009/0253130 | A1 * | 10/2009 | Yoo | 435/6 |
| 2010/0234237 | A1 * | 9/2010 | Yoo | 506/9 |
| 2010/0243078 | A1 * | 9/2010 | Yoo | 137/468 |
| 2010/0288949 | A1 * | 11/2010 | Yoo | 251/65 |

FOREIGN PATENT DOCUMENTS

| | | |
|---|---|---|
| CN | 1592684 | 3/2005 |
| CN | 2874467 | 2/2007 |
| KR | 10-2005-0118651 | 12/2005 |
| KR | 10-2008-0005224 | 1/2008 |
| WO | 2006/118420 | 11/2006 |

\* cited by examiner

*Primary Examiner* — Betty Forman
(74) *Attorney, Agent, or Firm* — Staas & Halsey LLP

(57) ABSTRACT

Disclosed herein is a thin-film layered centrifuge device and an analysis method using the same. One example of an embodiment of the present invention is a thin film layered centrifuge device where a device, such as a lab on a chip, a protein chip and a DNA chip, for diagnosing and detecting a small amount of material in a fluid is integrated into a rotatable thin-film layered body, and to an analysis method using the thin-film layered centrifuge device.

27 Claims, 23 Drawing Sheets the direction of the centrifugal force the direction of the centrifugal force

THIN-FILM LAYERED CENTRIFUGE DEVICE AND ANALYSIS METHOD USING THE SAME

BACKGROUND

1. Field

Embodiments of the present invention relate to a thin film layered centrifuge device and an analysis method using the same. More specifically, embodiments of the present invention relate to a thin film layered centrifuge device wherein a thin-film rotatable body is integrated with an apparatus to diagnose and detect a small amount of materials present in fluids, such as a lab-on-a-chip, a protein chip and a DNA chip, and an analysis method using the same.

2. Description of the Related Art

General clinical diagnosis and analysis apparatuses to detect a small amount of analytes in fluids include multiple sample arrangement and automated sample feed devices, and have a structure in which an apparatus to analyze a large number of test samples in series or parallel is integrated on a rotatable thin film body to improve analysis efficiency and economic efficiency. For example, rotatable bio discs are one type of such analyzers. Such thin-film analyzers for clinical tests enable various types of analysis to be performed accurately and automatically at a low cost, based on the centrifugal force generated by rotation of the bio disc, with a small amount of samples and specimens.

Considering thin film-type CDs and DVDs, standard compact discs can be formed from a 12 cm polycarbonate substrate, reflective metal layer and a protective layer coating. The format of CDs, DVD and CD-ROMs may be in accordance with ISO 9660 industrial standard. The polycarbonate substrate is made of optical-quality transparent polycarbonate. A data layer in standard printed or bulk-copied CDs is a part of the polycarbonate substrate and the data is printed by a stamper in the form of a series of pits during injection molding. Polycarbonate molten during the injection molding process is injected into a mold at a high pressure and is then cooled to obtain polycarbonate in the form of the mold, the stamper or a mirror-image thereof, and pits showing binary data on the disc substrate are formed on the polycarbonate substrate. The stamping master may be a glass. Such a disc may be modified into a thin film analyzer to diagnose and detect a small amount of material in a fluid. In this case, channels to allow flow of fluids, chambers to store buffer solutions, and holes or valves, may be formed on the surface of the disc instead of the pits.

Hereinafter, a disc wherein bio chips such as a lab-on-a-chip, a protein chip and DNA chip to diagnose and detect a small amount of materials in fluids are integrated in a disc such as a conventional CD-ROM or DVD, or a disc to perform biological and chemical processes to diagnose and detect a small amount of materials in fluids is referred to as a bio disc.

Conventional bio discs may include a plurality of chambers to store a large volume of liquid-phase biological and chemical materials required for chemical processes. The biological and chemical processes include preparing specimens from samples, centrifugation, DNA amplification, hybridization, antigen-antibody reactions, mixing, washing and the like. The biological and chemical processes may be sequentially automatically performed on the bio disc, which is known in the art. However, there is a need to solve the following problems associated with bio discs in order to make practical application possible.

For the process of centrifugation wherein specimens are extracted from samples, a valve, which does not leak during centrifugation, is required. Conventional valves to realize close/open operations based on physical movement perform the operations in such a manner that a ball or closing portion comes into contact with a hole or a channel, or the ball or closing portion is separated therefrom, which are known in the art. However, these valves inevitably allow opening based on physical movement, thus entailing incomplete closing. Accordingly, inherent hydraulic pressure of fluids may cause leakage during centrifugation. This leakage prevents extraction of desired amounts of specimens from samples by centrifugation, thus causing deterioration in assay reliability and accuracy. Accordingly, there is a need for a centrifuge device that does not leak during rapid rotation.

SUMMARY

Therefore, it is one aspect of the present invention to provide a thin film layered centrifuge device wherein a thin-film rotatable body is integrated with an apparatus to diagnose and detect a small amount of materials present in fluids, such as a lab-on-a-chip, a protein chip and a DNA chip, and an analysis method using the same. Embodiments provide a thin film centrifuge device in which bio chips, such as a lab-on-a-chip, protein chips and DNA chips, to diagnose and detect a material in a fluid are integrated, by providing a thin film body with a centrifuge device causing no leakage, when specimens are extracted from samples by centrifugation, and an analysis method using the same.

Additional aspects of the invention will be set forth in part in the description which follows and, in part, will be obvious from the description, or may be learned by practice of the invention.

In accordance with one aspect of the present invention, provided is a thin film centrifuge device including: a sample inlet to inject a sample; a sample chamber to store the sample injected into the sample inlet; a specimen chamber to store a specimen obtained from the sample during centrifugation; a remnant chamber to store a remnant rather than specimens produced during centrifugation; a bottle neck channel to connect the specimen chamber to the remnant chamber; one or more assay sites in which a capture probe to be bound to the specimen is immobilized and/or reagent for biochemical reactions with the specimen is stored; a trash chamber to collect debris not bound to the capture probe by a cleaning process; a rotatable hydrophobic body in which the sample inlet, the sample chamber, the specimen chamber, the remnant chamber, the trash chamber, the bottle neck channel and the assay site are integrated; one or more fluid flow devices to transfer the specimen from the specimen chamber to the assay site upon non-rotation of the body, the fluid flow devices selected from the group consisting of a hydrophilic fluid flow pump, a chamber pump, an erythrocyte pump and an absorption pump; and a liquid valve coated with a super-hydrophilic material, to provide a passage to connect the specimen chamber to the assay sites, allowing the specimen retained in the specimen chamber during centrifugation to flow to the assay site by the fluid flow device upon non-rotation of the body.

The liquid valve has a U- or V-shape to provide a hydrophilic channel to connect the specimen chamber to the assay site, when the body creases rotation, and at the same time to prevent transfer of the fluid in the specimen chamber to the assay site when the body rotates. The surface of the liquid valve is treated with a super-hydrophilic material and the fluid trapped in the specimen chamber when the body rotates can be transferred to the assay site via hydrophilic fluid flow by the liquid valve when the body ceases rotation. In one embodiment, by using the channel having a superhydrophilic-coated U- or V-shape channel as the liquid valve, all the specimens in the specimen chamber can hydrophilic-flow to the assay site, when the body ceases rotation.

In one embodiment, volume of the total specimen in the specimen chamber, required for quantitative analysis can be determined. Accordingly, the embodiment comprises transfer of the total specimen from the specimen chamber to the assay site. However, the specimen present in the specimen chamber, having a viscosity comparable to blood serum may be partially transferred through the U- or V-shaped channel to the assay site due to inherent viscosity. That is, when the body ceases rotation, through the U- or V-shaped hydrophilic channel, only a part of the specimen in the specimen chamber may be transferred to the assay site, thus making quantitative analysis impossible. Accordingly, in one embodiment, in order to transfer the total specimen from the specimen chamber to the assay site, when the body ceases rotation, a fluid flow means may be provided to the specimen in the specimen chamber.

In one embodiment, the specimen in the specimen chamber can be entirely transferred to the assay site using the following four fluid flow means.

First, the remnant chamber swollen while the body rotates is returned, and, at the same time, generates air pressure, when the body ceases rotation. This air pressure may generate fluid-driving force to transfer the total specimen from the specimen chamber to the assay site. Hereinafter, a fluid flow means based on fluid-driving force generated by swelling and return of the remnant chamber is referred to as a chamber pump. When the body rotates, the swelling of the remnant chamber may be caused by centrifugal force. The remnant chamber is arranged farther from the circumference than the specimen chamber and stores a material heavier than the specimen, for example, erythrocyte, according to one embodiment, and the upper base material of the remnant chamber may swell during this high-speed rotation. The upper base material of the remnant chamber may be a thin film having a thickness of 0.1 mm to 0.6 mm, enabling easy swelling during high-speed rotation.

Second, the material in the remnant chamber compressed while the body rotates, for example, erythrocyte according to one embodiment, is expended and at the same time, generates a fluid pressure, when the body creases rotation. The fluid pressure specimen chamber may generate fluid-driving force to transfer the total specimen from the specimen chamber to the assay site. Hereinafter, fluid flow means using fluid-driving force based on compression and expansion of erythrocyte in the remnant chamber is referred to as an erythrocyte pump. When the body rotates, compression of erythrocyte in the remnant chamber may be generated by centrifugal force.

Third, an absorption force to absorb the specimen having reached the terminal of the liquid valve through the U- or V-shaped hydrophilic channel including an absorbent pad, a sample pad, or a super-hydrophilic chamber between the terminal of the liquid valve and an inlet of the assay site continuously generates fluid-driving force to transfer the total specimen from the specimen chamber to the assay site or super-hydrophilic chamber. Hereinafter, a fluid flow means using fluid-driving force based on absorption force of the absorbent pad or the sample pad or hydrophilic absorption force of the super-hydrophilic chamber is referred to as an absorption pump.

Fourth, by coating the U- or V-shaped channel with a super-hydrophilic material, hydrophilic absorption force to transfer the specimen from the specimen chamber to the assay site can generate fluid-driving force to transfer the total specimen from the specimen chamber to the assay site. Hereinafter, a fluid flow means based on fluid-driving force derived from the hydrophilic absorption force is referred to as hydrophilic fluid flow.

In one embodiment, by transferring the total specimen in the specimen chamber to the assay site via the fluid flow means, the specimen chamber can be emptied. After the total specimen is discharged from the specimen chamber through the liquid valve to the assay site, the fluids are not transferred from the remnant chamber to the liquid valve due to strong capillary action of the bottle neck channel to fluids. That is, strong capillary action of the bottle neck channel to fluids may be equivalent to fluid flow force of the fluid flow means, preventing further transfer of the fluids to the assay site. Accordingly, only quantitative specimen is transferred to the assay site.

In one embodiment, the chamber pump, the erythrocyte pump, the absorption pump and fluid flow means via hydrophilic fluid flow may further utilize fluid-driving force based on capillary force obtained from the U- or V-shaped channel.

In one embodiment, the sample chamber may be coated with a super-hydrophilic material. In one embodiment, the super-hydrophilic coating includes hydrophilic coating.

In one embodiment, the sample includes various biomaterials, for example, blood. In addition, the specimen includes substances obtained from a sample by centrifugation, for example, blood serum or plasma obtained from blood.

In exemplary embodiments, the term "blood serum" used herein is intended to include the blood serum, plasma and leukocytes.

In one embodiment, the remnant chamber may be a capillary tube chamber.

When blood is centrifuged, it is separated into blood serum, blood clotting factors, plasma and erythrocytes. The blood clotting factors may be mostly erythrocyte. Accordingly, when blood of the sample chamber is stored, and the specimen chamber and the remnant chamber are centrifuged, blood serum is left in the specimen chamber and erythrocyte is left in the remnant chamber. In this case, when the rotation is ceased after centrifugation, erythrocyte may be admixed with blood serum again. That is, rotation of the body should be stopped in order to extract only blood serum after centrifugation. In this case, erythrocyte is admixed with blood serum again, making extraction of only blood serum difficult. Accordingly, in one embodiment, the remnant chamber is provided as a capillary tube chamber having a low height (narrow), to allow erythrocyte to remain in the remnant chamber based on capillary action or bonding force between the surface of the remnant chamber, thereby preventing re-admixing of erythrocyte with blood serum. The bonding force between the surface of the remnant chamber and erythrocyte is based on strong viscosity of the erythrocyte. As a result, centrifuged erythrocyte is not admixed with blood serum and is thus left in the remnant chamber although the body ceases rotation. The height of the capillary tube chamber may be, for example, 0.1 mm to 0.6 mm.

In one embodiment, the body may further comprise a cleaning chamber to store a cleaning solution required for cleaning.

In one embodiment, the body may further comprise a mixing chamber to mix the two fluids.

In one embodiment, the body may further comprise a buffer chamber to store a dilution buffer to dilute the specimen or a label to be linked to a target material in the specimen. The label may have antibody- or DNA-linked chromatic particles such as gold or gold conjugates, latex or fluorescent labels, radioisotopes, enzymes, or enzyme-linked antibody labels. The enzyme may render color using a substrate solution reacted with an enzyme.

In one embodiment, the body may further comprise a substrate chamber to store the substrate solution reacted with the enzyme.

In one embodiment, the specimen comprises biomaterials participating in biochemical bonding, such as blood serum, DNA, proteins, ligands or receptors.

In one embodiment, the thin film centrifuge device may further comprise a thin film cylindrical magnet to perform azimuthal direction search of the assay site in the body. Instead of the thin film cylindrical magnet, thin-film ferromagnetic metal particles may be used. The thin film cylindrical magnet or thin film ferromagnetic metal particles may have a diameter of 1 mm to 5 mm and a thickness of 0.1 mm to 1 mm.

In one embodiment, the bottle neck channel may be composed of two thin film channels. The bottle neck channel provides a passage to transfer the remnant from the specimen chamber to the remnant chamber, or to transfer the centrifuged analyte from the remnant chamber to the specimen chamber, while the sample in the specimen chamber and the sample in the remnant chamber are independently centrifuged by centrifugal force generated by rotation of the body. That is, the bottle neck channel may provide a passage, allowing the analyte and remnant separated during centrifugation to be transferred from the specimen chamber to the remnant chamber.

In one embodiment, the remnant chamber has no outlet. That is, the remnant chamber has no channel or outlet, to allow liquids to flow in or leak out, except the bottle neck channel. The bottle neck channel is provided in a thin film channel, preventing return of the remnant from the remnant chamber to the specimen chamber when the body ceases rotation, and maintaining a predetermined amount of the specimen in the specimen chamber. That is, when the body stops, strong capillary action of the bottle neck channel composed of the thin film channel and absence of outlet in the remnant chamber make it impossible to freely transfer the fluids from the remnant chamber to the specimen chamber. In addition, after the total specimen is discharged from the specimen chamber through the liquid valve via hydrophilic fluid flow, the fluids in the remnant chamber do not transfer to the liquid valve due to strong capillary action of the bottle neck channel to fluids. That is, strong capillary action of the bottle neck channel to fluids is equivalent to the force of hydrophilic fluid flow to induce transfer to the liquid valve, preventing further transfer of fluids to the liquid valve.

In one embodiment, the hydrophilic channel may be treated via surface modification using a porous material, or coated with a water-based paint or a super-hydrophilic paint.

In one embodiment, the thin film centrifuge device may further comprise a spindle motor to rotate the body.

The thin film centrifuge device according to one embodiment comprises a bio pickup optical module (BOPM) mounted on a slider and a slide motor to control movement of the BOPM, enabling space addressing of the chambers. A laser beam generator and a permanent magnet are mounted on the BOPM, and coordinates of the BOPM may be moved or controlled by control of the slide motor. The laser beam generator uses, for example, an optical pick-up device. The radial direction search may be carried out by control of the slide motor. The azimuthal direction search is carried out by rotating the body to some extent, while controlling short rotation of the spindle motor or the stepper motor, when the slider is stopped. The stepper motor may be connected or mounted to a gear on the shaft of the spindle motor for azimuthal direction rotation of the body.

The thin film centrifuge device may further comprise a temperature-control means to control reaction temperatures of the chambers. The temperature-control means may comprise at least one selected from the group consisting of temperature-measurement means, heating means and cooling means. The heating means comprises a laser beam generator mounted on the slider. The cooling means may perform rotation-cooling using rotation of body. Heat emission efficiently occurs due to contact between the surface of the chamber and air during rotation of the body. The temperature measurement means may measure the temperature of the corresponding chamber using the temperature sensor connected to the wireless RF IC provided in the body and wirelessly transmit the temperature to the outside central control device.

The body comprises a rotatable thin film disc, composed of an upper base material, an intermediate base material and a lower base material. For example, the disc has a diameter of 120 mm, 80 mm or 32 mm, a thickness of 0.6 mm to 3 mm and a circular shape.

The flow of fluids may be carried out by centrifugal force or capillary action generated by rotation force of the body phenomenon, or using a super-hydrophilic-coated channel.

The body may be selected from various materials such as plastics, glasses, silicon wafers or hydrophobic materials. However, plastics are preferred, owing to economical efficiency, processability, and compatibility with conventional laser reflection-based detectors such as CD-ROM and DVD detectors. The substrate is composed of at least one selected from the group consisting of silicon wafers, polypropylene, polyacylate, polyvinylalcohol, polyethylene, polymethyl methacrylate (PMMA), cyclic olefin copolymers (COCs) and polycarbonate. In addition, the body may be coated with aluminum to prevent evaporation of liquids stored in the chamber.

The body may be composed of an upper base material, an intermediate base material and a lower base material. These materials may be adhered to one another by an adhesive agent. The adhesive agent may be prepared from a material selected from the group consisting of silicon, rubbers, modified silicon, acrylic, polyester and epoxy.

The body is composed of an upper base material, an intermediate base material and a lower base material which are laminated in this order and adhered to one another and further comprises a first thin film adhesive to adhere the upper base material to the intermediate base material, and a second thin film adhesive to adhere the intermediate base material to the lower base material. The thin film adhesive tape may be a one-side tape or two-side tape. The tape is obtained by surface-treating one or both sides of release papers such as papers, vinyl polyester films, polyethylene films and other synthetic materials with an adhesive (or a gluing) agent. According to requirements, adhesive materials exhibiting properties such as superior sealing, buffering, vibration reduction, impact resistance, heat resistance, absorbent performance or adhesion force may be used. The thin film adhesive tape may be prepared via thin film coating on one side of a substrate using an adhesive agent, performed by adhering an one-side tape to the substrate and removing a release paper therefrom, or printing a dispenser, spraying or silk screen printing on one side of the substrate. That is, in one embodiment, the thin film adhesive tape may be coated on the substrate in the form of a thin film using an adhesive (gluing) agent without any release paper.

The device may further comprise magnetic micro-beads contained in the mixing chamber; a slider movable in a lower part of the body; and a permanent magnet mounted on the slider, to apply attraction force to the magnetic micro-beads and thus move the magnetic micro-beads, wherein the magnetic micro-beads are moved in accordance with movement of the slider to induce mixing of liquids in the mixing chamber.

In another embodiment, the device may further comprise magnetic micro-beads contained in the mixing chamber; a slider movable in a lower part of the body, and a permanent magnet mounted on the slider, to apply attraction force to the magnetic micro-beads and thus move the magnetic micro-beads, wherein the magnetic micro-beads are moved in accordance with movement of the slider, by keeping the permanent magnet on the corresponding diameter of the mixing chamber and rotating the body, to induce mixing of liquids in the mixing chamber.

In one embodiment, the mixing operation may be performed prior to radial direction search, or radial direction search and azimuthal direction search of the mixing chamber to perform the mixing operation.

In one embodiment, the specimen chamber may further comprise a set-amount channel connected to the remnant chamber, to transfer excess fluid.

The assay site may store reagents for biochemical reaction or include a porous membrane on which a capture probe is fixed. The assay site may comprise a porous membrane; a capture probe fixed on the porous membrane; a capture probe spotted and fixed in an array on the substrate; micro-pores formed on the substrate, or a capture probe fixed on the micro-pores. The assay site comprises a porous membrane and line- or spot-shaped tumor markers or disease labels fixed on the porous membrane as a test line, the porous membrane may be in the form of a strip, allowing lateral flow or flow through. The porous membrane is provided at one terminal with a sample pad and a conjugate pad, at the other terminal with an absorbent pad. The tumor label or disease label may be AFP, PSA, CEA, CA19-9, CA125, CA15-3 or Alzheimer markers, or myocardial infarction label.

The assay site may further comprise a capture probe for a reference line and a control line fixed on the porous membrane. The reaction concentration of the reference line may be a cutoff value. For example, the cutoff concentration of the reference line may be 3 ng/ml, 4 ng/ml, 10 ng/ml, 20 ng/ml, 30 ng/ml, 40 ng/ml or 50 ng/ml. For example, qualitative or quantitative analysis can be realized based on the difference in reaction intensity between the reference line and the test line. For example, qualitative or quantitative analysis can be realized based on the difference in reaction intensity between the background of the strip and the test line. For example, qualitative or quantitative analysis can be realized by determining reaction intensity of test lines using the linear function of reaction intensity formed by the plurality of reference lines. Qualitative or quantitative analysis can be realized by determining reaction intensity of test lines using a linear function of reaction intensity formed by the reference line and the control line.

The body may comprise a wireless RF IC to measure temperature, detect assay sites, store and transmit the assay site detection results and perform personal privacy encryption. The thin film centrifuge device may further comprise a detector to detect the reaction results of the assay site. The detector may be a spectrometer including a light source and a photo-detector. In addition, the detector may be an optical measurement apparatus including an illuminator and an image sensor (for example, CCD, CMOS, or CIS sensors). Alternatively, the detector may be a photometric measurement apparatus comprising a laser beam apparatus and a photodetector.

The thin film layered centrifuge device and an analysis method using the same according to one embodiment may be applied to thin-film devices to diagnose and detect a small amount of biological and/or chemical materials in fluids such as a lab-on-a-chip, protein chips and DNA chips. For example, the thin film centrifuge device may be integrated in thin film discs such as conventional CD-ROMs or DVDs.

The thin film layered centrifuge device and an analysis method using the same according to one embodiment may be applied to lab-on-a-chips utilizing ELISA/CLISA analysis methods, lab-on-a-chips utilizing rapid test methods; or thin-film devices to diagnose and detect a small amount of biological and/or chemical materials in fluids, such as lab-on-a-chips for food poisoning-causing bacteria assays, residual antibiotic assays, residual pesticide assays, genetically modified food tests, food allergy tests, contaminant assays or paternity tests, and meat types and origin region tests. The residual pesticide comprises pesticide contained in vegetables or fruits, for example, the most-generally used organophosphorus and carbamate insecticides.

In one embodiment, the biomaterial may be at least one selected from DNA, oligonucleotides, RNA, PNA, ligands, receptors, antibodies, antibodies, milk, urine, saliva, hairs, crop samples, meat samples, fish samples, bird samples, wastewater, livestock samples, food samples, oral cells, tissue samples, semen, proteins or other biomaterials.

Upon urine assay, the thin film centrifuge device may perform leukocyte, blood, protein, nitrite, pH, specific gravity, glucose, ketone, ascorbic acid, urobilinogen and bilirubin assays.

Hair assays accurately measure historical record of nutriment and toxic substances including minerals accumulated in blood or urine assays. Hair assays accurately detect oversupply and lack of inorganic materials for a long time and provide a standard to assay the amount of toxic heavy metals, which is known in the art.

In accordance with another aspect of the present invention, provided is an analysis method using a thin film centrifuge device including: a sample inlet to inject a sample; a sample chamber to store the sample injected into the sample inlet; a specimen chamber to store a specimen obtained from the sample during centrifugation; a remnant chamber to store a remnant rather than specimens produced during centrifugation; a bottle neck channel to connect the specimen chamber to the remnant chamber; an excess chamber to store excess specimen exceeding a predetermined amount of the specimen chamber; one or more assay sites in which a capture probe to be bound to the specimen is immobilized and/or reagent for biochemical reactions with the specimen is stored; a liquid valve coated with a super-hydrophilic material, the liquid valve formed on a passage to connect the specimen chamber to the assay sites; a trash chamber to collect debris not bound to the capture probe by a cleaning process; and a rotatable hydrophobic body in which the sample inlet, the sample chamber, the specimen chamber, the excess chamber, the trash chamber, the bottle neck channel and the assay sites are integrated; the method including: injecting a sample into the sample chamber through the sample inlet; transferring the sample from the sample chamber to the specimen chamber and the remnant chamber based on centrifugal force generated by rotation of the body and moving the residual sample to the remnant chamber, when the sample is present in an amount exceeding a predetermined level of the specimen chamber; centrifuging the sample in the specimen chamber and the remnant chamber based on centrifugal force generated by rotation of the body, and at the same time, transferring the remnant present in the specimen chamber through the bottle neck channel to the remnant chamber, or the specimen from the remnant chamber through the bottle neck channel to the specimen chamber; hydrophilic-flowing the specimen retained in the specimen chamber through the liquid valve to the assay site when the body ceases rotation; and binding the specimen present in the assay site to the capture probe present in the assay site, or biochemically reacting the specimen with a reagent in the assay site.

The analysis method may further include adding the cleaning solution to clean the assay site, and drying and dehydrating the assay site.

The analysis method may further include one or more operations selected from: searching an assay site; qualitatively or quantitatively analyzing reaction results of the assay site; allowing the wireless RF IC integrated in the body to detect the assay site to realize wireless transmission; displaying diagnosis results derived from the analysis on a computer monitor; and remote-transmitting diagnosis results and questionnaires to a doctor connected through an internet network; or obtaining the doctor's prescription.

The analysis method may further include moving magnetic micro-beads in the mixing chamber via magnetic force to mix the liquid in the mixing chamber.

The analysis method may further include preventing fluid leakage from the specimen chamber by centrifugal force using a liquid valve having a U- or V-shape based on the rotation center of the body, while the body rotates.

The analysis method may further include controlling the temperature of the assay site using the temperature-control means.

The analysis method may further include searching a specific one selected from the plurality of assay sites and selecting the same; and detecting the response of the specific assay site. The detection process may be carried out using a spectrometer. The detection of the assay site using the spectrometer may be carried out after searching the chamber through controlling the rotation angle of the body using the stepper motors or gears connected thereto or through the azimuthal valve search process, or by sequentially measuring light absorption in the respective assay sites during rotation of the body through space-addressing assay sites using a blank solution chamber during rotation of the body.

The light source or light source device of the spectrometer may be a white light LED, an RGB laser, or an LD module in which a plurality of laser diodes (LDs) are integrated.

The detection of the assay site using the spectrometer may include; passing specific wavelengths of light from the light source device of the spectrometer through the upper base material in the body, or the assay site in which a reflective layer is integrated; and detecting light reflected by the reflective layer using the photodetector to measure light absorption of the specimen in the assay site. The detection of the assay site using the spectrometer may include measuring light absorption of the specimen using the photodetector integrated in the body to obtain detection results, and receiving the detection results using the wireless RF IC integrated in the body to wirelessly transmit the results.

The cleaning process may further include adding a cleaning solution to the assay site to clean the assay site. The cleaning process may further include drying and dehydrating the assay site based on centrifugal force caused by rotation of the body. The remnant (debris) formed in the drying and dehydrating processes may be trapped in the trash chamber based on centrifugal force.

In one embodiment, the body may include: a preparation chamber to prepare DNA or RNA from blood serum obtained from the specimen chamber; an amplification chamber to amplify the DNA and RNA; and a fragmentation chamber to fragment the amplified DNA to a predetermined length. For example, the DNA cut in a predetermined size in the fragmentation chamber is incorporated into the assay site in which DNA capture probes are arranged in an array and is hybridized with the DNA capture probes having a complementary sequence to produce double stranded DNA. Various embodiments to detect hybridization are known in the art. The thin film centrifuge device may further include, in addition to the chamber, a chamber required for DNA amplification and fragmentation processes.

In one embodiment, the thin-film centrifuge device may further include a thin film cylindrical magnet to perform space-addressing of the amplification chamber or the fragmentation chamber in the body.

In one embodiment, the thin-film centrifuge device may further include a heating means to heat the amplification chamber or the fragmentation chamber and a cooling means to cool the same.

In one embodiment, the amplification chamber includes performing a thermo cycle using polymerase chain reaction (PCR). The space-addressing the amplification chamber or the fragmentation chamber using the heating means may be carried out through radial direction search and azimuthal direction search.

The analysis method may further include: isolating DNA or RNA in the preparation chamber; fragmenting the amplified DNA to a predetermined length; and labeling a marker on one terminal of DNA.

The DNA amplification process may further include rotation-cooling based on high-speed rotation of the body.

In one embodiment, the fragmentation process may further include: incorporating DNAse in the amplification chamber after DNA amplification; heating the DNAse using the heating means to inactivate DNAse (incubation); and/or producing single stranded DNA (denaturing).

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
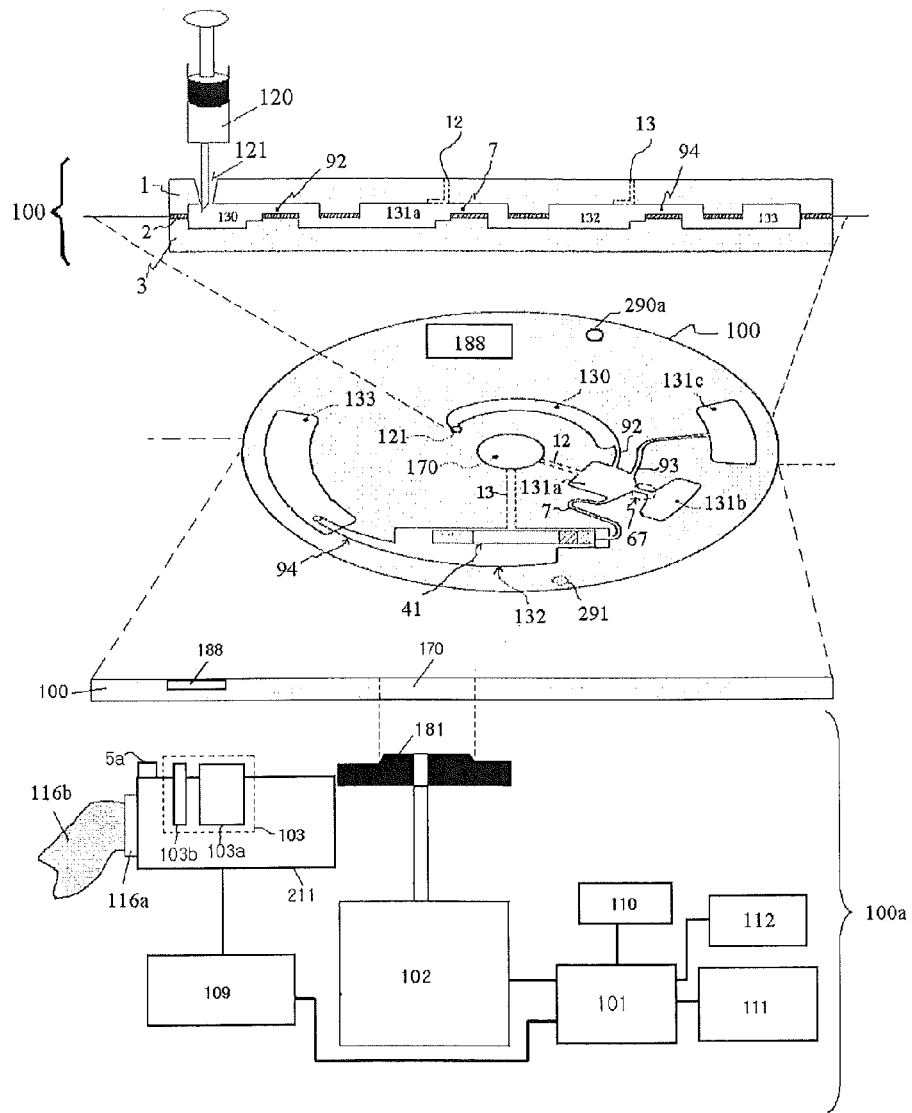
FIGS. 1 and 2 are a sectional view and a plan view illustrating a thin film layered centrifuge device and a thin film layered centrifuge device drive to control operation of the device according to one embodiment of the present invention.

Reference will now be made in detail to the embodiments of the present invention, examples of which are illustrated in the accompanying drawings, wherein like reference numerals refer to like elements throughout.

Reference will now be made in detail to the embodiments of the present invention, examples of which are illustrated in the accompanying drawings, wherein like reference numerals refer to like elements throughout.

Figure 2:
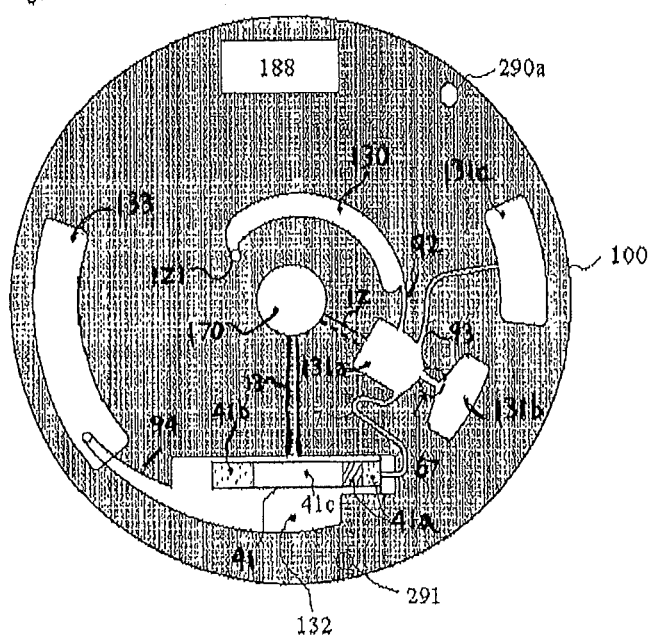

FIGS. 1 and 2 are a sectional view and a plan view illustrating a thin film layered centrifuge device and a thin film layered centrifuge device drive to control operation of the device according to one embodiment of the present invention.

Referring to FIGS. 1 and 2, the thin film centrifuge device may be realized by integrating a lab-on-a-chip in thin film devices such as conventional disc devices including CD-ROMs and DVDs. For example, in one embodiment, provided are a thin film centrifuge device 100 in which one or more chambers 130, 131a, 131b, 131c and 133 to store various buffer solutions required for analysis and to perform various chemical processes and centrifugation, channels 92, 93 and 67 to enable the buffer solutions to be transferred, an assay site 132 and a liquid valve 7 are integrated on a thin film disc; and a thin film layered centrifuge device drive 100a to control operation of the device.

As shown in FIG. 1, reference numeral 100 means a thin film centrifuge device, which includes a body or a base material, formed by laminating an upper base material 1, an intermediate base material 2 and a lower base material 3. The thin film centrifuge device also includes: the channels 92, 93 and 67 to allow fluids to flow on the respective base materials during injection molding; a liquid valve 7; a sample chamber 130; a specimen chamber 131a; a remnant chamber 131b; an excess chamber 131c; an assay site 132 and a trash chamber 133. These elements are closely adhered to one another to constitute the thin film centrifuge device 100.

In one embodiment, the thin film centrifuge device may further include an outlet 12 to discharge atmospheric pressure generated by transferring samples from the specimen chamber 131a to the sample chamber 130. The outlet 12 may be arranged opposite to the direction of centrifugal force. In another embodiment, outlets 12 and 13 and a bottle neck channel 67 may be formed by a thin film channel.

In one embodiment, the thin film channel may be formed between the base materials 1, 2 and 3 by a channel-shaped thin-film adhesive tape. That is, the base materials 1, 2 and 3 are adhered to one another by a thin film adhesive tape to constitute the thin film centrifuge device 100, and the thin film channels may be provided in a region provided between the base materials in which the thin film tape is omitted. The thickness of the thin film channels may be determined depending on the thickness of the thin film adhesive tape. Due to low thickness of the thin film channels, strong capillary action to fluids may occur. In one embodiment, the thickness of the thin film adhesive tape may be, for example, 0.001 mm to 0.1 mm.

Hereinafter, one embodiment wherein a sample is blood is illustrated with reference to FIGS. 1 and 2.

Reference numeral 120 indicates a dispenser, a pipette, a syringe, a lancet or a sample injection means to incorporate a sample, reference numeral 121 indicates a sample inlet, reference numeral 170 indicates a disc hole.

Reference numeral 130 indicates a sample chamber to store blood injected from the sample inlet. Blood present in the sample chamber 130 is transferred through the channel 92 to the specimen chamber 131a and the remnant chamber 131b, while the body 100 initially rotates, and excess blood is transferred through set-amount channels 93 to the excess chamber 131c. Then, centrifugal force caused by rotation of the body 100 causes independent centrifugation of blood stored in the specimen chamber 131a and the remnant chamber 131b, thus separating blood present in the remnant chamber 131b as well as in the specimen chamber 131a into blood serum and erythrocytes.

Reference numeral 67 indicates a bottle neck channel to connect the specimen chamber 131a to the remnant chamber 131b. The bottle neck channel 67 provides a passage, allowing transfer of the erythrocytes present in the specimen chamber 131a to the remnant chamber 131b and of the blood serum present in the remnant chamber 131b to the specimen chamber 131a, when bloods present in the specimen chamber 131a and the remnant chamber 131b are centrifuged by the centrifugal force generated by rotation of the body 100. That is, the bottle neck channel 67 provides a passage, enabling blood serum and erythrocyte to be freely moved from the specimen chamber 131a to the remnant chamber 131b during centrifugation. As shown in FIG. 1, the remnant chamber 131b is arranged close to the external circumference of the body, as compared to the specimen chamber 131a. For this reason, as a result of movement of blood serum and erythrocyte through the bottle neck channel 67, erythrocyte is collected in the remnant chamber 131b and blood serum is collected in the specimen chamber 131a.

The bottle neck channel 67 may be composed of two thin film channels for collection of blood serum and erythrocyte during centrifugation. For such a bottle neck channel 67 composed of two thin film channels, the remnant chamber 131b need not be provided with an additional outlet. That is, the outlet 13 of the specimen chamber 131a also acts as an outlet of the remnant chamber 131b by the centrifugal force generated during rotation of the body 100. However, the outlet 13 of the specimen chamber 131a cannot act as an outlet of the remnant chamber 131b due to the absence of centrifugal force when the body 100 is not rotated.

Although blood is centrifuged well, erythrocyte may be admixed with blood serum again, when the body ceases rotation. That is, in order to selectively extract only blood serum after centrifugation, the body 100 should cease rotation. In this case, erythrocyte is admixed with blood serum again, making it difficult to extract only pure blood serum. In order to prevent this problem, primarily, the specimen chamber 131*a* is isolated from the remnant chamber 131*b* and secondarily, the bottle neck channel 67 is interposed between the specimen chamber 131*a* and the remnant chamber 131*b* to prevent fluid transfer therebetween, thirdly, the remnant chamber 131*b* is provide in the form of a capillary tube with a low height (narrow) to allow erythrocyte to remain in the remnant chamber 131*b* due to inherent capillary action of the remnant chamber 131*b* or bonding force between the surface of the remnant chamber 131*b* and erythrocyte, thus preventing admixing of the erythrocyte with blood serum in the specimen chamber 131*a*. The bonding force between the surface of the remnant chamber 131*b* and erythrocyte is derived from strong viscosity of erythrocyte. When the remnant chamber 131*b* is in the form of a capillary tube, centrifuged erythrocyte is not admixed with blood serum even when the body is not rotated and remains on the surface of the remnant chamber 131*b*. Accordingly, the blood serum in the specimen chamber 131*a* is not admixed with erythrocyte and maintains its state even upon non-rotation of the body.

In one embodiment, the excess chamber 131*c* transfers residual (excess) blood through the set-amount channel 93 to the excess chamber 131*c* by centrifugal force generated by rotation of the body 100. Depending on control of thickness of the set-amount channel 93, the amount of blood (or blood serum) remaining in the specimen chamber 131*a* may be determined. The blood having a height higher than the thickness of the set-amount channel 93 may be transferred through the set-amount channel 93 to the excess chamber 131*c* by centrifugal force generated by rotation of the body 100.

Reference numeral 290*a* is a base hole for alignment required for producing and assembling the thin film centrifuge device 100. The base hole 290*a* is injected into a fixture provided in a jig.

Reference numeral 132 indicates an assay site in which a capture probe for bonding (for example, biological specific binding) to blood serum in the specimen chamber 131*a* is fixed, and/or reagents for reactions (for example, biochemical reactions) with specimens are stored.

Reference numeral 41 indicates a porous membrane or strip on which the capture probe provided in the assay site 132 is fixed. Reference numeral 13 is an outlet provided in the assay site 132, which generates air stream upon rapid rotation of the body 100 to promote drying of the strip 41. Prior to washing, the strip 41 is dried to promote diffusion of a washing solution on the strip during the washing and wash background noise-causing ingredients due to diffusion force.

Blood serum trapped in the specimen chamber 131*a* during centrifugation may be transferred through the liquid valve 7 to the assay site 132 based on hydrophilic fluid flows when the body 100 ceases rotation.

Reference numeral 133 indicates a trash chamber to collect debris generated by washing. That is, debris which does not bond to the capture probe of the assay site 132 during rapid rotation of the body 100 is trapped in the trash chamber 133 via the channel 94.

Reference numeral 211 indicates a slider equipped with a permanent magnet 5*a*, which is connected to a slide motor 109 for operation control.

The fluid flows are realized by the centrifugal force derived from rotational force of the body, or super-hydrophilic coatings of channels.

Reference numeral 291 indicates a thin-film cylindrical magnet to spatially address the assay site 132.

Reference numeral 103*a* indicates an optical pick-up device to read conventional optical discs (for example, CDs or DVDs), reference numeral 103*b* is a detection device of the assay site 132 for quantitatively or qualitatively analyzing the assay site 132, which may be a light transmission measurement apparatus, a fluorescence detection device, an image sensor, a spectrophotometer or a surface plasmon resonance (SPR) detection device, and the optical pick-up device 103*a* and the assay site detection device 103*b* constitute a bio optical pickup module (BOPM) device 103. Various embodiments of the fluorescence detection devices and SPR detection devices are known in the art.

In one embodiment, the thin film centrifuge device for space-addressing the assay site 132 includes the bio pickup optical module (BOPM) device 103 equipped on the slider 211 and a slide motor 109 to control movement of the BOPM device 103. A permanent magnet 5*a* is mounted on the slider 211, to attract the thin film cylindrical magnet 291, and movement of coordinates of BOPM device can be controlled by control of the slide motor 109. The space addressing to the assay site 132 may be realized by radial and azimuthal direction search.

One embodiment of the radial and azimuthal direction search is as follows. The radial direction search is a process for transferring the permanent magnet 5*a* in a radial direction, which is carried out by moving the permanent magnet 5*a* on the slider 211 on the corresponding diameter of the thin film cylindrical magnet 291. Then, the azimuthal direction search is required to overlap the permanent magnet 5*a* and the thin film cylindrical magnet 291 on the corresponding diameter. The azimuthal direction search is carried out by slowly rotating a spindle motor 102 or repeatedly operating short rotation and stop of the same, while the slider 211 is stopped. During slow rotation or several short rotation of the spindle motor, the permanent magnet 5*a* on the slider 211 corresponds to the thin-film cylindrical magnet 291 present on the corresponding diameter, the body 100 cannot be rotated by slow or short rotation due to strong attraction force therebetween. In this case, the permanent magnet 5*a* and the thin film cylindrical magnet 291 are aligned.

In addition, in another embodiment, the azimuthal direction search may be carried out by controlling rotation of stepper motors which are mechanically connected to the shaft of the spindle motor 102 in need of the azimuthal direction search. The rotation of the stepper motors enables control of the rotation angle of the spindle motor 102.

Reference numeral 116*b* indicates a flexible cable to connect control signals required for BOPM 103 on the slider 211, which is connected to a central control device 101 through a wafer or a harness 116*a*.

Reference numeral 181 is a turn table on which the thin film centrifuge device 100 is placed, and the thin film centrifuge device 100 is placed in front of or on the top of the turn table through a central hole 170 of the body. Reference numeral 188 indicates a memory-provided wireless RF IC or an electric tag device, which includes protocols for lab-on-a-chip processes, detection results of the assay site 132, analysis algorithm, standard control values for detection, and location information of the assay site 132, information associated with bioinformatics, and information associated with self diagnosis. In addition, the memory-provided wireless RF IC or an electric tag device may store personal privacy encryption information, and identification (ID) of the thin film centrifuge device, thus preventing others' use without permission. The wireless RF IC 188 includes a smart IC card. The information of the wireless RF IC 188 is supplied to the central control device 101 through wireless transmission/reception and may thus be utilized in personal privacy encryption. Reference numeral 110 indicates a wireless electric wave generator to supply power to the wireless RF IC 188. An alternating magnetic field generated by the wireless electric wave generator 110 senses an induction coil provided in the wireless RF IC 188 in accordance with Fleming's rule, to generate a sufficient amount of electricity and supply the same to the wireless RF IC 188. The wireless electric wave generator is provided with a multipole permanent magnet to generate electricity on the induction coil provided in the wireless RF IC 188 based on an alternating magnetic field generated by rotation of the body 100. In one embodiment, the multipole permanent magnet may be circumferentially arranged on a tray to load the body 100.

For the thin film centrifuge device according to one embodiment, the wireless RF IC 188 performs temperature measurement to measure the temperature of the assay site 132 and wirelessly-transmits the same to the central control device 101. The assay site 132 can maintain a constant temperature using a heating or cooling apparatus, when the temperature is excessively high or low. In one embodiment, the temperature of the assay site 132 is within the range of 30 to 37 degrees in the reaction with specimens, for example, in which biochemical activity and stability are considered.

For the thin-film centrifuge device according to one embodiment, the wireless RF IC 188 may include information such as test date and test results according to residual pesticide and antibiotic tests of the thin film centrifuge device, efficient periods, agriculture and stockbreeding regions, production and farming (culturing) history, distribution history, contact information of farmers, price and organic products. Consumers and agriculture and stockbreeding distribution enterprises may purchase crops and livestock products with ease using the information. General consumers can obtain information by touching the thin film centrifuge device 100 to the RF IC detector, or loading the same on the thin film centrifuge drive 100*a*.

For the thin film centrifuge device according to one embodiment, the wireless RF IC 188 can store the test results of the thin film centrifuge device in a memory provided therein.

For the thin film centrifuge device according to one embodiment, the wireless RF IC 188 controls the detection device of the assay site, and wirelessly transmits the results thus obtained to the central control device 101 or a storage device 112 or an input/output device 111.

For the thin film centrifuge device according to one embodiment, the input/output device may be a universal serial bus (USB) or IEEE1394 or ATAPI or SCSI or a device having a communication standard of internet network. In addition, user information, such as height, weight, gender and age, of the thin film centrifuge device 100 can be input through the input/output device 111.

FIG. 2 illustrates an absorption pump provided between the terminal of the liquid valve 7 and the assay site 132 with a sample pad 41*a* or an absorption pad 41*b* to transfer blood serum in the specimen chamber 131*a* to the assay site 132 by an absorption force to absorb blood serum in the specimen chamber 131*a* through a U- or V-shaped hydrophilic channel 7 according to one embodiment. The specimen chamber 131*a* can be emptied by transferring blood serum in the specimen chamber 131*a* to the assay site 132 via the absorption pump. After specimens present in the specimen chamber 131*a* are ejected through the liquid valve 7 to the assay site 132, fluids in the remnant chamber 131*b* do not transfer to the liquid valve 7 due to strong capillary action of the bottle neck channel 67. That is, strong capillary action of the bottle neck channel 67 to fluids is equivalent to the fluid movement force of the absorption pump and the fluid does not transfer to the assay site 132. Reference numeral 41*b* indicates an absorption pad, reference numeral 41*a* indicates a sample pad and a conjugate pad, and these pads are connected to the terminals of a porous membrane 41*c*.

Figure 3:
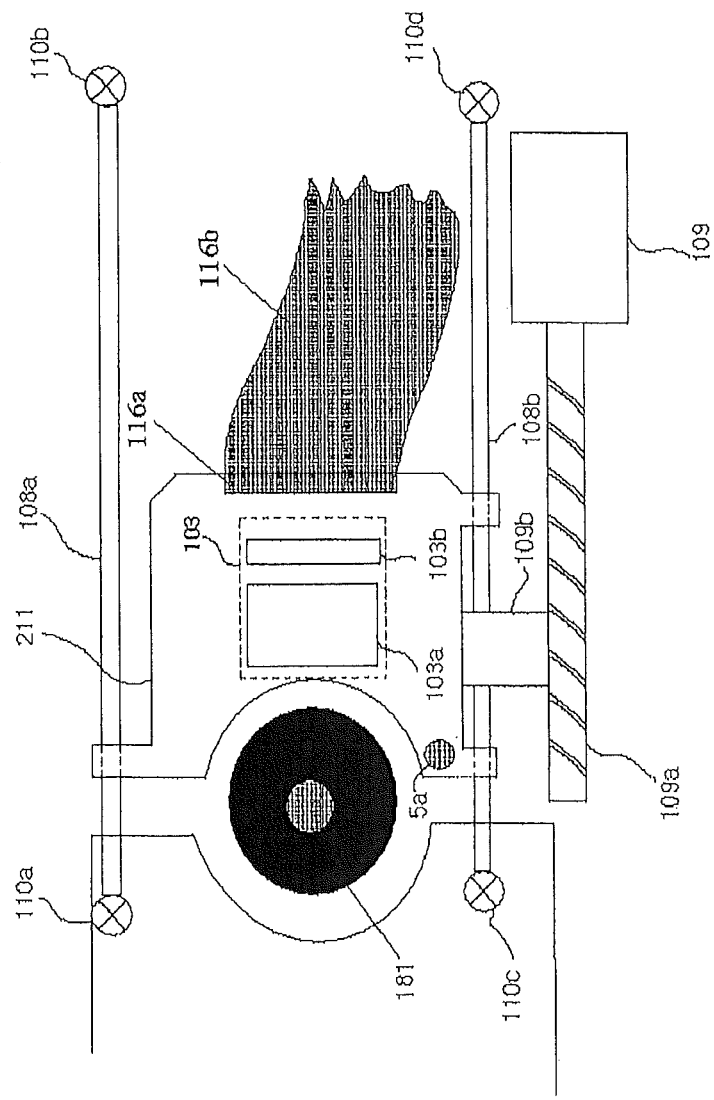
FIG. 3 is a top view illustrating a slider provided with a BOPM and a permanent magnet according to one embodiment of the present invention.

FIG. 3 is a top view illustrating a slider provided with a BOPM 103 and a permanent magnet 5*a* according to one embodiment of the present invention. The movement of the slider can be controlled by worm gear connections 109*a* and 109*b* connected to the shaft of a slide motor 109. The slider may slide using slide arms 108*a* and 108*b* as guides. The slide arms 108*a* and 108*b* are engaged through screws 110*a*, 110*b*, 110*c* and 110*d* on the body of the thin film layered centrifuge device (100*a*, shown in FIG. 1). Reference numeral 116*b* indicates a flexible cable, which is connected through a wafer or a harness 116*a*. Reference numeral 181 indicates a turn table rotated by the spindle motor (102, shown in FIG. 1).

Figure 4:
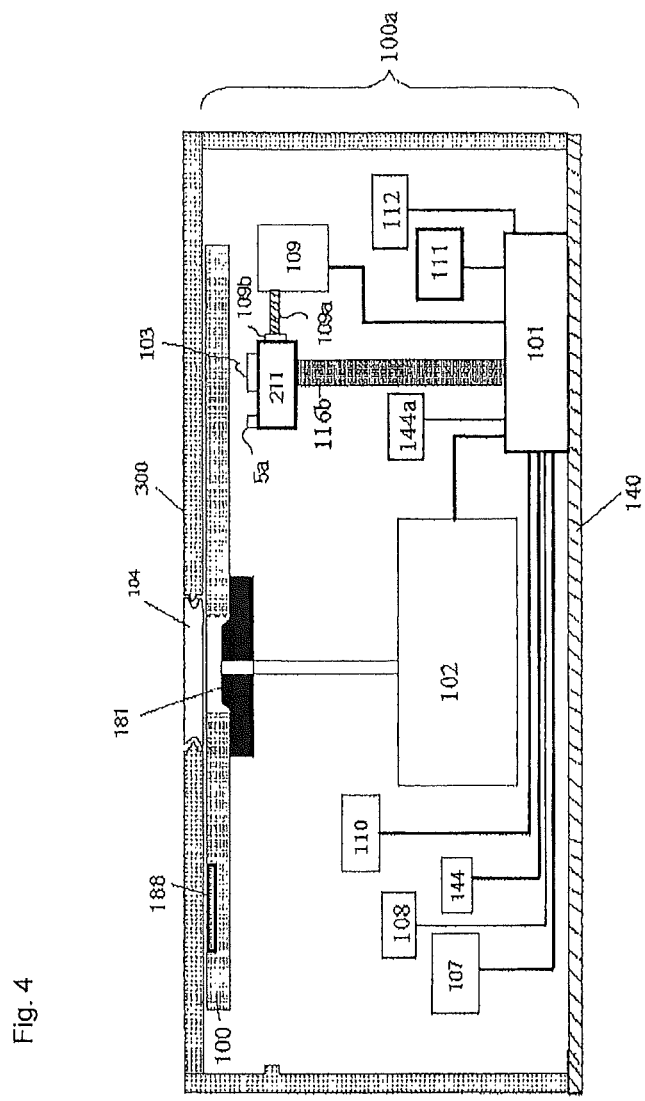
FIG. 4 is a side view illustrating a thin film layered centrifuge device drive to operate and control the thin film centrifuge device of FIG. 1 according to one embodiment of the present invention.

FIG. 4 is a side view illustrating a film layered centrifuge device drive 100*a* to operate and control the thin film centrifuge device 100 of FIG. 1 according to one embodiment of the present invention. Reference numeral 300 indicates a body to support the thin film layered centrifuge device drive 100*a*. A circuit substrate 140 is continuously engaged in the body 300 of the thin film layered centrifuge device drive under the thin film layered centrifuge device drive, and the central control device 101, the storage device 112 and the input/output device 111 to control the thin film layered centrifuge device drive 100*a* are arranged on the circuit substrate 140. The central control device 101 controls a spindle motor 102 to rotate and brake the thin film centrifuge device 100, controls movement of the bio optical pickup module (BOPM) arranged on the slider 211 by control of the slide motor 109, and moves the permanent magnet 5*a* for space-addressing the assay site 132 of the thin film centrifuge device 100. The permanent magnet 5*a* can efficiently transfer an electric field to a thin film-type cylindrical magnet (291, see FIG. 1). In addition, the central control device 101 decides whether the disc loaded on the thin film layered centrifuge device drive 100*a* is a conventional optical disc (for example, music CDs, CD-Rs, and game CDs/DVDs) or the thin film centrifuge device 100. When the disc is a conventional optical disc, the device 101 transfers information read from the disc from the optical pick-up device (103*a*, see FIG. 3) to the storage device 112 or input/output device 111, transfers data to be written to the optical pick-up device (103*a*, see FIG. 3), or performs conventional operations for optical discs, for example, supplies various control signals required for reading and writing to respective elements.

In one embodiment, upon loading of the thin film centrifuge device, inherent ID of the thin film centrifuge device 100 is wirelessly transmitted to the central control device 101 through the wireless RF IC 188 on the thin film layered centrifuge device to inform the central control device 101 of the fact that the disc loaded on the thin film layered centrifuge device drive 100*a* is a thin film centrifuge device.

In one embodiment, detection results associated with the assay site 132 are transferred via wireless communication through the wireless RF IC 188 provided on the thin film centrifuge device 100 to the central control device 101, the storage device 112 or the input/output device 111. The detection associated with the assay site 132 may be carried out by transferring image information associated with the assay site 132 obtained by an image sensor 144 arranged on the circuit substrate 140 to the central control device 101 or storage device 112 or input/output device 111. Reference numeral 104 is a compression device of the thin film centrifuge device 100 loaded on a disc hole, which performs compression by means of attraction force, based on a magnetic field with a turn table 181 and is designed such that vertical movement and no-load rotation are allowed.

Reference numeral 144a indicates one or more light-emitting diodes (LEDs) to illuminate the image sensor, the image sensor 144 or the LED 144a is mounted on the slider 211 or equipped on or under the assay site 132. In one embodiment, the LEDs include multi-color LEDs to emit various wavelengths of light, which can obtain reaction intensity of the assay site 132 as image information represented by color intensity under illumination of various wavelengths, and enables quantitative or qualitative analysis of response results of the assay site 132 based on 2-dimensional correlation between the wavelengths and color intensity. The multicolor LEDs include R, G and B LEDs. Reference numeral 107 indicates a laser beam generator used to excite fluorescently labeled specimens in the assay site. In this case, the image sensor 144 enables image information associated with the assay site to be obtained. Reference numeral 108 indicates a spectrophotometer, which outputs a plurality of light wavelengths to measure light transmission or light absorption of the assay site and measures light transmission or light absorption of respective wavelengths to detect reaction results of the assay site 132. A spectrometer generally includes a light source, a wavelength selector, a specimen vessel (test tube or assay site 132), and a photodetector, which is known in the art. A spectrometer measures light absorbance of the specimen solution of the assay site, after it is calibrated using a blank solution such that light transmission is 100% (light absorbance of 0%). A light source should uniformly emit a sufficient energy of light required for specimen analysis. Examples of the light source that can be used in the present invention include tungsten filament lamps, hydrogen or deuterium lamps, white light LEDs and lasers. In one embodiment, the light source may be an LD module in which white light LEDs or RGB lasers or a plurality of laser diodes (LDs) are integrated. The RGB laser is a module device comprising 3 lasers to emit red, green and blue light. Combining various powers of these lasers enables generation of various wavelengths of light required for specimen analysis. The LD module is a module of a plurality of laser diodes (LDs) having different wavelengths. In accordance with the LD module, light absorbance of the specimen at the corresponding wavelengths of light are measured, while LDs to output the corresponding wavelength of light are sequentially turned on. For the spectrometer, it is important to obtain specific wavelength of radiation from the light emitted from the light source. Monochromatic radiation is ideal, but in practice, this is very difficult. Accordingly, for light showing a predetermined range of wavelength distribution, monochromatization level can be represented by specifying the spectrum band width. Sensitivity and resolution of measurement are proportional to the closeness of the light emitted from the light source to a single wavelength. The desired wavelength of light can be obtained using a wavelength selector and the wavelength selector may be a filter or a grating mirror or a combination thereof. The grating mirror acts as a prism to distribute and reflect incident light at various wavelengths.

Figure 5:
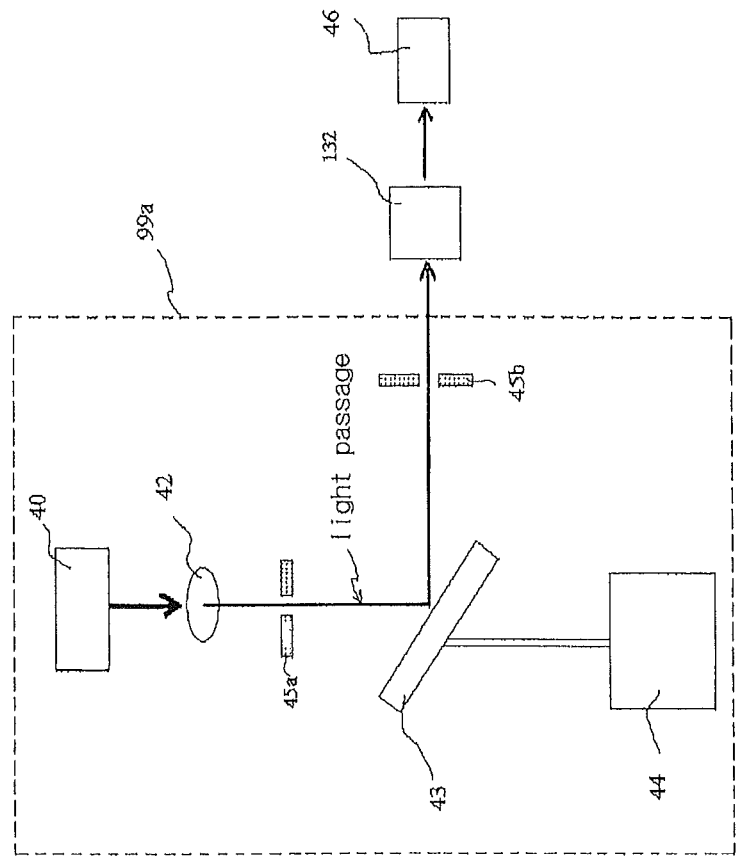
FIG. 5 illustrates a spectrometer using a grating mirror according to one embodiment of the present invention.

FIG. 5 illustrates a spectrometer (108, See FIG. 4) using a grating mirror according to one embodiment of the present invention.

As shown in FIG. 5, white light emitted from a light source 40 passes through a lens 42, converges into a beam, and passes through a primary H-slit and a V-slit 45a to generate a spot beam. When the spot beam is incident on a grating mirror 43, light reflected from the grating mirror 43 is separated into different wavelengths in a topological space. In order to collect specific wavelengths from the light reflected from the grating mirror 43 and separated in the topological space, a secondary H-slit and V-slit 45b is set at a specific angle. In this case, the wavelengths of light passing through the secondary H-slit and V-slit 45b can be varied by rotating the grating mirror 43. That is, the desired specific wavelengths of light can be obtained by controlling the rotation angle of the grating mirror 43.

After the specific wavelengths of light thus obtained pass through the assay site 132, the photodetector 46 measures light absorption, light transmission or color intensity of the specimen in the analysis site to perform qualitative or quantitative analysis of reaction results of the site specimen. Methods for qualitatively or quantitatively analyzing the reaction results of the specimen include an end point, rate assay, initial rate methods, or the like, which are known in the art.

Reference numeral 40 indicates a light source of the spectrometer 108 and the wavelength selector includes a stepper motor 44 to control the rotation angle of the grating mirror 43, a lens 42 to converge light generated from the light source and the primary H-slit and V-slit 45a to convert the converged beam into a spot beam, the grating mirror 43 to separate the spot beam into various wavelengths, and the secondary H-slit and V-slit 45b to pass only a specific angle of beam (that is, specific wavelengths of light) reflected from the grating mirror 43. The specific wavelengths of light obtained by the light source 40 and the wavelength selector pass through the assay site 132 and light absorption of the specimen present in the assay site is measured with the photodetector 46, to qualitatively or quantitatively analyze reaction results of the specimen. Light absorption of the specimen in the assay site can be measured at various wavelengths by passing various wavelengths of light through the assay site 132, while rotating the stepper motor 44.

In one embodiment, an optical fiber may be used instead of the primary H-slit and V-slit or secondary H-slit and V-slit.

In one embodiment, hereinafter, one of various combinations of the light source, the lens, the primary H-slit and V-slit or the primary optical fiber 45a, the grating mirror 43, the secondary H-slit and V-slit 45b or secondary optical fiber will be referred to as a light source device 99a. The LD module and the RGB laser module may singly constitute the light source device 99a. In this case, the light source device 99a may be simplified.

Figure 6:
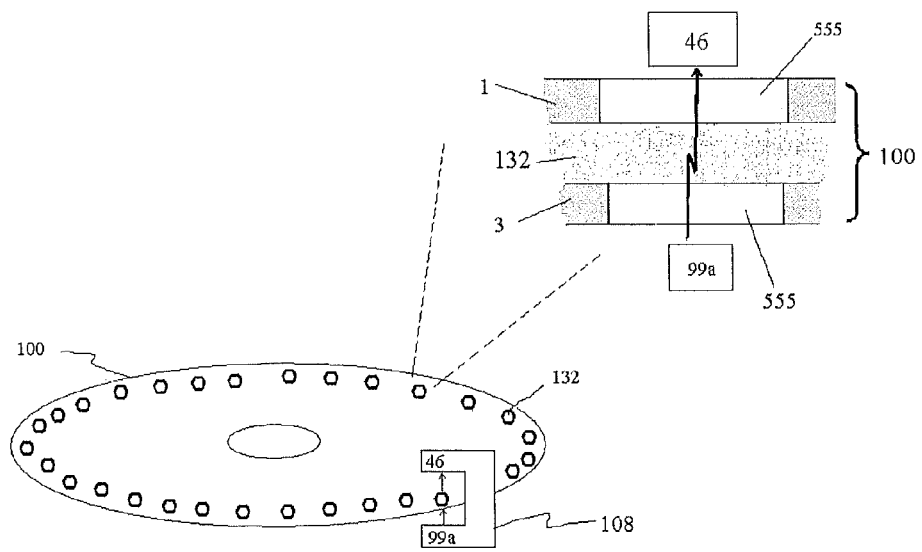
FIGS. 6 to 8 illustrate a method for detecting the assay site using a spectrometer on the thin film centrifuge device according to one embodiment of the present invention.
Figure 7:
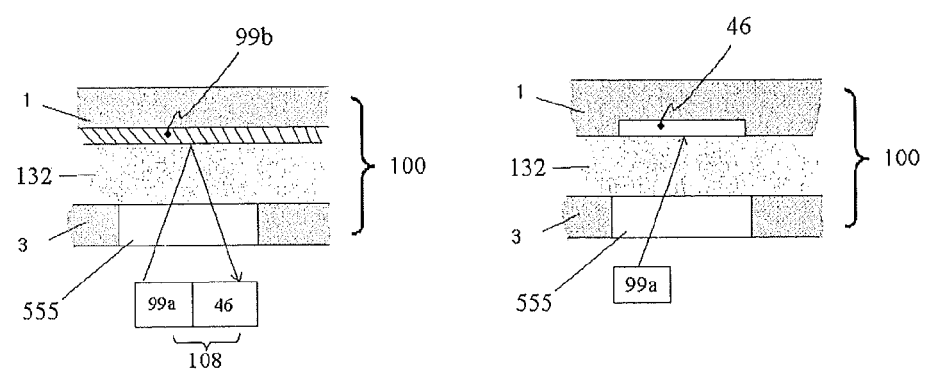
Figure 8:
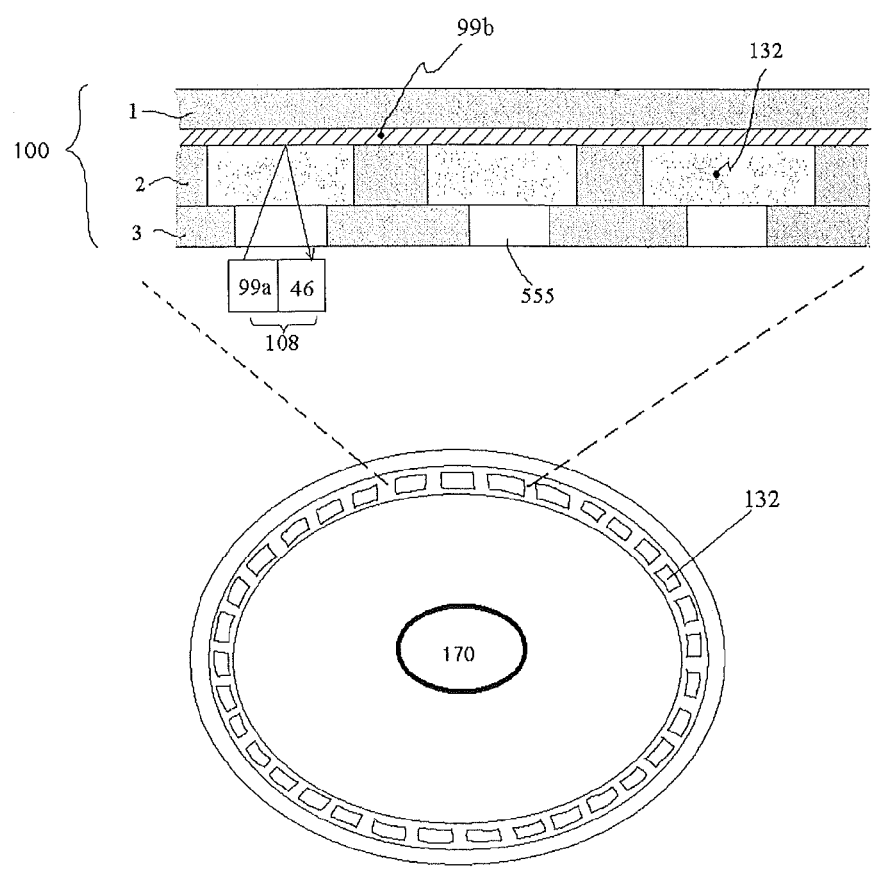

FIGS. 6 to 8 illustrate a method for detecting the assay site 132 using a spectrometer 108 on the thin film centrifuge device 100 according to one embodiment of the present invention. Reference numeral 555 indicates a transparent opening to detect the photodetector 46.

As shown in FIG. 6, the photodetector 46 of the spectrometer 108 is arranged on the thin film centrifuge device 100 and the light source device 99a is arranged thereunder. A plurality of assay sites 132 arranged in a circumferential direction in the thin film centrifuge device 100 are detected using the spectrometer 108 in which the light source device 99a and the photodetector 46 are modulated. In this case, as the thin film centrifuge device 100 rotates, one to one correspondence occurs between the spectrometer 108 and each of the assay sites 132 provided in a circumferential direction in the thin film centrifuge device 100, thus realizing space addressing and detection. The measurement of light absorbance of the specimen solution in the plurality of assay sites using the spectrometer 108 is performed, after the device is calibrated using a blank solution such that light transmission reaches 100% (light absorbance: 0). In one embodiment, one or more of the plurality of assay sites may include a blank solution chamber for calibration.

As can be seen from the left image of FIG. 7, a reflective layer 99b is integrated in an upper base material 1 or an assay site in the thin film centrifuge device 100, and the spectrometer 108 in which the light source device 99a and the photodetector 46 are modulated in a lower side of the thin film centrifuge device 100 is arranged. The specific wavelengths of light obtained from the light source device 99a pass through the assay site 132 and the photodetector 46 measures light reflected from the reflective layer 99b, to measure light absorption of the specimen in the assay site.

The right image of FIG. 7 shows a case in which the photodetectors 46 are integrated in the assay sites 132 of the thin film centrifuge device 100. In this case, the photodetectors 46 are arranged such that they correspond one-to-one to the plurality of assay sites 132. When the photodetectors 46 are integrated in the thin film centrifuge device 100, the optical path is shortened, reception sensitivity of the photodetectors 46 increases and sensitivity is improved. The detection results of the photodetectors 46 integrated in the thin film centrifuge device 100 are read by the wireless RF IC 188 and are then wirelessly transmitted to the central control device (101, see FIG. 1).

As shown in FIG. 8, the reflective layer 99b illustrated in the left image of FIG. 7 is integrated in an upper base material 1, and a plurality of assay sites (132, see FIG. 7) are arranged in a circumferential direction of the thin film centrifuge device 100. The spectrometer 108 one-to-one corresponds to each of the assay sites provided in a circumferential direction in the thin film centrifuge device 100 to realize sequential detection by space-addressing. In this case, the light source device 99a emits wavelengths of light suitable for the specimen in the respective assay sites 132, to measure light absorbance. In one embodiment, space-addressing of the assay site by radial direction search and azimuthal direction search performed by mounting the spectrometers 108 on the slider 211 may be performed prior to sequential detection of the assay sites 132 using the spectrometers 108. The image sensor includes a CCD, a CMOS and a line image sensor for sensing light amount in pixel units. In one embodiment, the line image sensor includes a linear sensor array or a contact image sensor (CIS). In one embodiment, the BOPM 103 including the image sensor can move the slider 211 to obtain image information of the assay site. Prior to detection of the assay site, space-addressing of the assay site by radial direction search and azimuthal direction search performed by mounting the spectrometers 108 on the slider 211 may be performed.

Figure 9:
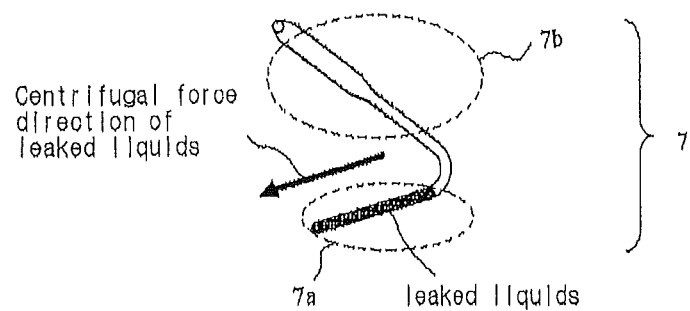
FIGS. 9 and 10 illustrate a liquid valve to prevent liquid leakage during centrifugation according to one embodiment of the present invention.
Figure 10:
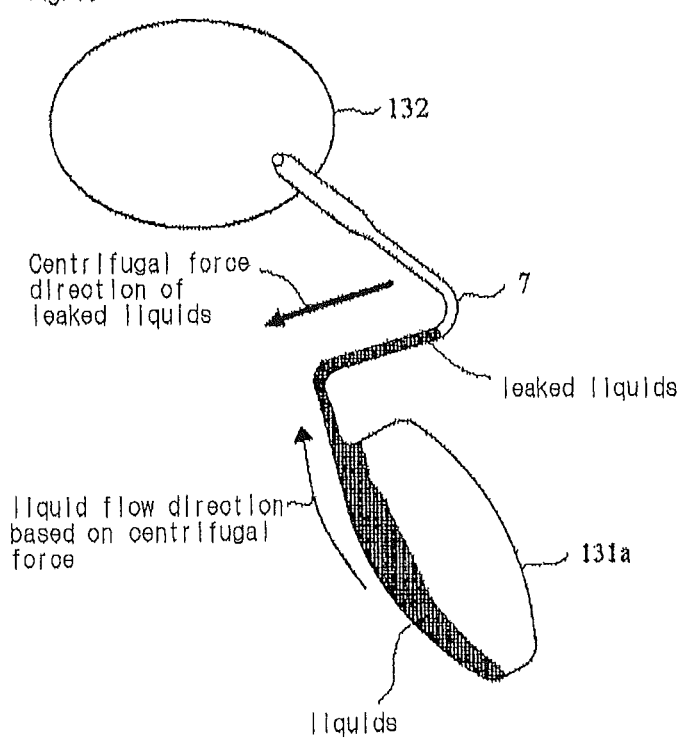

FIGS. 9 and 10 illustrate a liquid valve to prevent liquid leakage during centrifugation according to one embodiment of the present invention. The liquid valve 7 prevents transfer of blood serum to the assay site 132 through a V- or U-shaped channel 7 upon high-speed rotation of the body 100. In addition, FIGS. 9 and 10 are detailed views of the liquid valve 7. The liquid valve 7 is broadly divided into two parts, i.e., an inward channel 7a and an outward channel 7b. The inward channel 7a refers to a channel extended toward the center of the body (opposite to a direction of the centrifugal force) and the outward channel 7b refers to a channel extended toward the centrifugal force direction. The operation of the liquid valve 7 is as follows. When the body 100 rotates at a high speed, the liquid leaked from the specimen chamber 131a is primarily charged in the inward channel 7a. Once the leaked liquid fills the inward channel 7a, centrifugal force acts in a radial direction toward the liquid contained in the inward channel 7a, thus preventing further leakage of the liquid from the specimen chamber 131a. Otherwise, the leaked liquid is withdrawn to the specimen chamber 131a by centrifugal force. That is, when liquid is leaked from the specimen chamber 131a upon high-speed rotation of the body 100, further leakage of the liquid can be prevented due to the equivalence between the force to further leak the liquid from the specimen chamber 131a and centrifugal force inherently acting on the already leaked liquid. This prevention of the leakage of liquid based on the centrifugal force acting on the leaked liquid is referred to as a liquid valve operation in one embodiment of the present invention.

In one embodiment, the specimen chamber 131a may further be provided at an outlet thereof with a liquid valve to prevent liquid leakage during centrifugation.

In one embodiment, the liquid valve includes liquid valves realized by a V- or U-shaped channel or a super-hydrophilic coated channel to operate the liquid valve.

Figure 11:
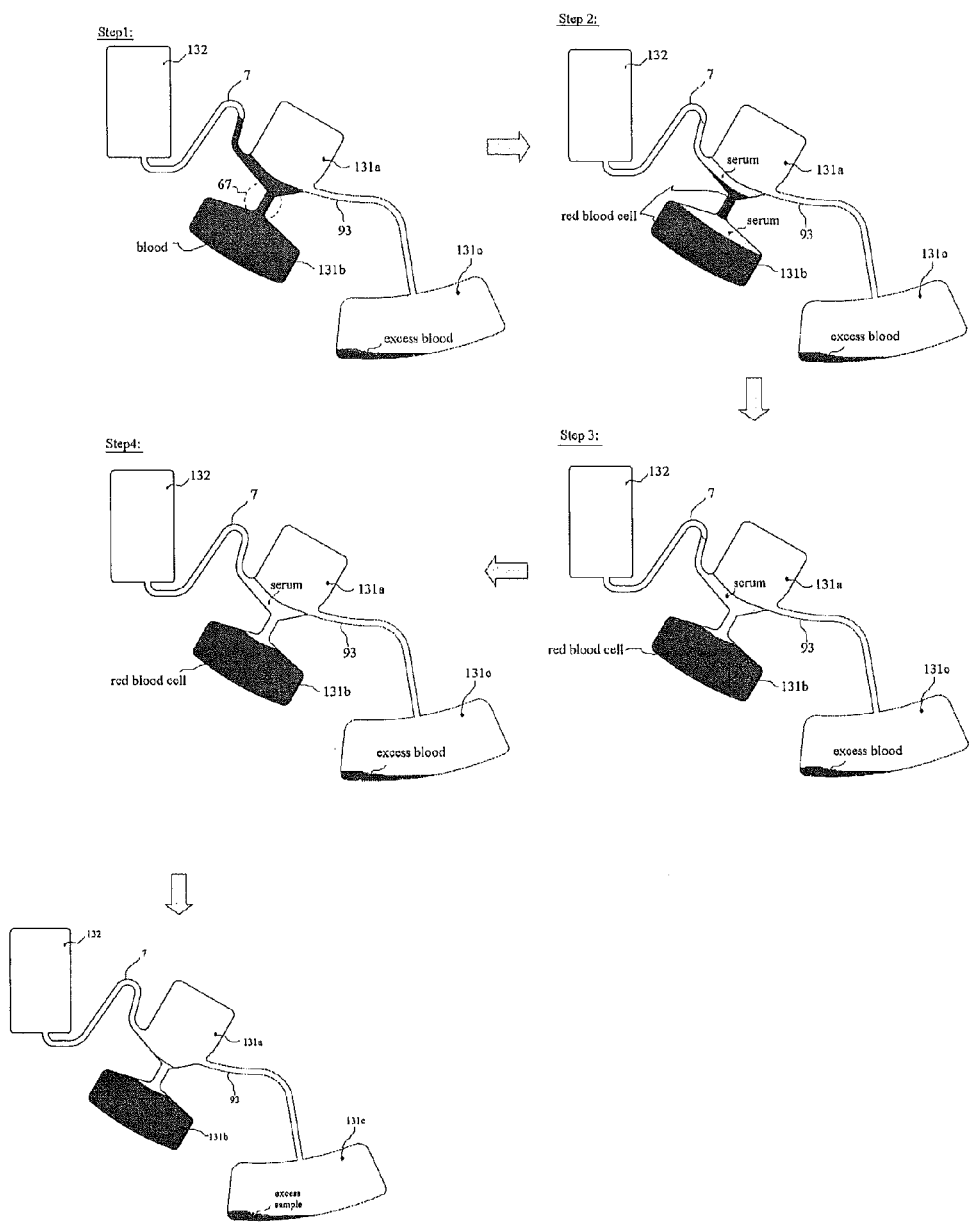
FIG. 11 illustrates a stepwise centrifugation process.

FIG. 11 is an image showing the specimen chamber 131a and the remnant chamber 131b of the thin film centrifuge device 100 of FIG. 2, for illustration of a centrifugation process.

FIG. 11 illustrates a stepwise process in which the blood transferred from the sample chamber 130 to the specimen chamber 131a and the remnant chamber 131b by rotation of the body 100 is separated into blood serum and erythrocyte by centrifugation. In step 1, blood is transferred from the sample chamber 130 to the specimen chamber 131a and the remnant chamber 131b during initial rotation of the body and blood having a height higher than the height of a set-amount channel 93 is moved to the excess chamber 131c by centrifugal force. In addition, blood cannot be moved through the liquid valve 7 to the assay site 132 and is thus retained in the specimen chamber 131a. Step 2 is an intermediate state of centrifugation, in which blood present in the specimen chamber 131a and blood present in the remnant chamber 131b are independently centrifuged, based on centrifugal force caused by rotation of the body and is thus separated into blood serum and erythrocyte. The centrifugal force caused by rotation of the body induces independent centrifugation of blood in the specimen chamber 131a and the remnant chamber 131b and allows erythrocyte in the specimen chamber 131a to be moved through the bottle neck channel 67 to the remnant chamber 131b. In addition, blood serum centrifuged in the remnant chamber 131b is moved through the bottle neck channel 67 into the specimen chamber 131a. That is, the bottle neck channel 67 provides a passage, allowing blood serum and erythrocyte separated during centrifugation to be smoothly moved from the specimen chamber 131a to the remnant chamber 131b. The remnant chamber 131b is arranged closer to the circumference than the specimen chamber 131a. For this reason, as a result of centrifugation, erythrocyte is collected in the remnant chamber 131b and blood serum is collected in the specimen chamber 131. Step 3 shows, as a result of Step 2, a state in which erythrocyte is collected in the remnant chamber 131b and blood serum is collected in the specimen chamber 131 after centrifugation. In step 4, the blood serum of the specimen chamber 131 hydrophilic-flows through the liquid valve 7 to the assay site 132, when the body 10 does not rotate after centrifugation. In step 5, only a predetermined amount of blood serum in the specimen chamber 131a is moved to the assay site 132. That is, only the predetermined amount of blood serum is moved to the assay site 132 and fluids present in the bottle neck channel 67 and the remnant chamber 131b are not moved to the assay site 132 and remain therein. The amount of blood serum moved to the assay site 132 is determined by the amount of blood serum stored in the specimen chamber 131a.

Such a phenomenon is due to the following five causes.

The bottle neck channel 67 is used as the thin film channel, strong capillary action occurs when the body is not rotated, the fluids present in the remnant chamber 131b are not moved through the bottle neck channel 67 to the specimen chamber 131a. Accordingly, transfer of erythrocyte from the remnant chamber 131b to the specimen chamber 131a can be prevented. The remnant chamber 131b is provided in the form of a capillary tube chamber and erythrocyte stored therein cannot be thus readily ejected. The bonding force between the surface of the remnant chamber 131b and the erythrocyte inhibits easy escape of erythrocyte from the remnant chamber 131b. When the body 100 does not rotate, the bottle neck channel 67 is clogged by viscose blood serum, thus making movement of erythrocyte stored in the remnant chamber 131b difficult. The remnant chamber 131b has no outlet, thus making movement of erythrocyte stored therein difficult.

Figure 12:
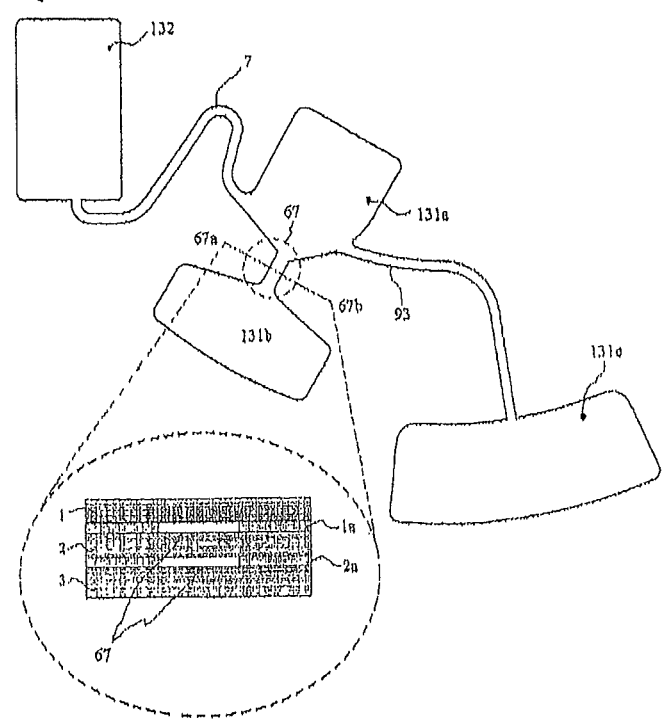
FIG. 12 illustrates a bottle neck channel according to one embodiment.

FIG. 12 illustrates a bottle neck channel 67 according to one embodiment. This detailed view illustrates a cross-section of the bottle neck channel 67, based on a base line to join reference numerals 67a and 67b.

The bottle neck channel 67 is composed of two thin film channels, which are formed by a first thin film adhesive tape 1a to join an upper base material 1 to an intermediate base material 2 and a second thin film adhesive tape 2a to join an intermediate base material 2 to a lower base material 3. The bottle neck channel 67 by formed by these two thin film channels provides a passage, enabling easy transfer of erythrocyte from the specimen chamber 131a to the remnant chamber 131b, or of blood serum from the remnant chamber 131b to the specimen chamber 131a during centrifugation. That is, the bottle neck channel 67 serves as a bottle neck channel to prevent fluid transfer upon non-rotation of the body and as a passage for blood serum and erythrocyte during centrifugation.

Figure 13:
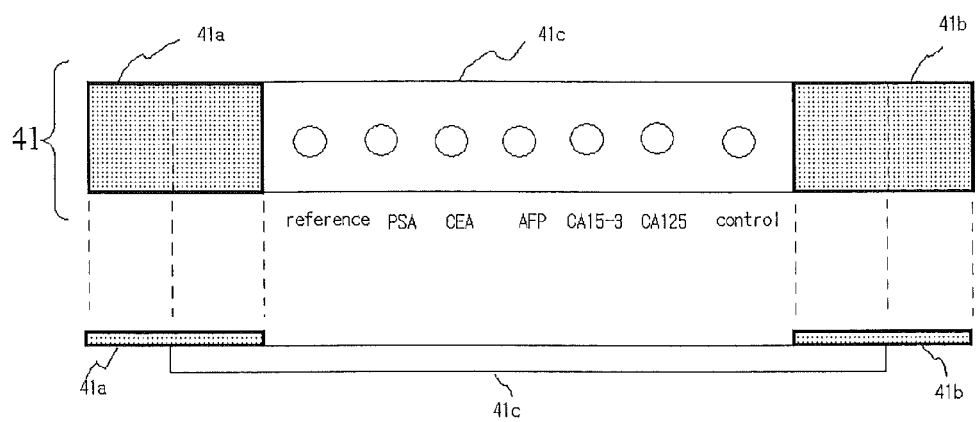
FIGS. 13 to 15 illustrate strips wherein various species of tumor markers are fixed in the form of a line or spot on the porous membrane according to one embodiment.
Figure 14:
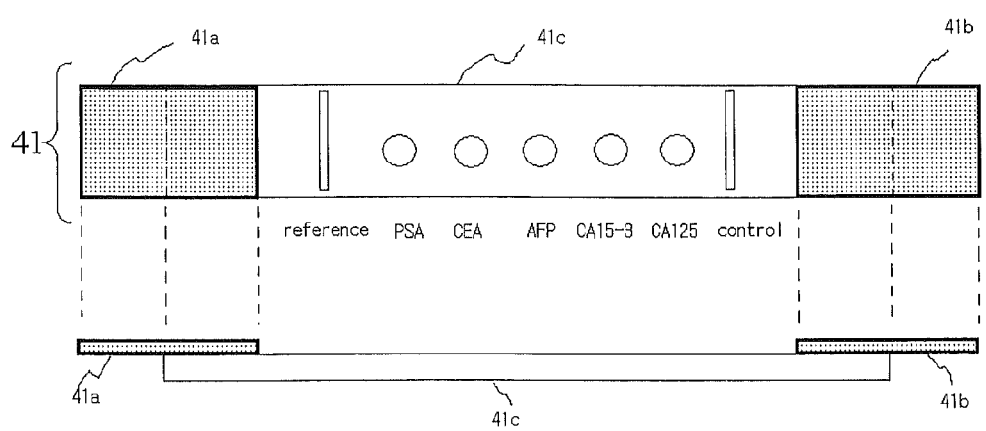
Figure 15:
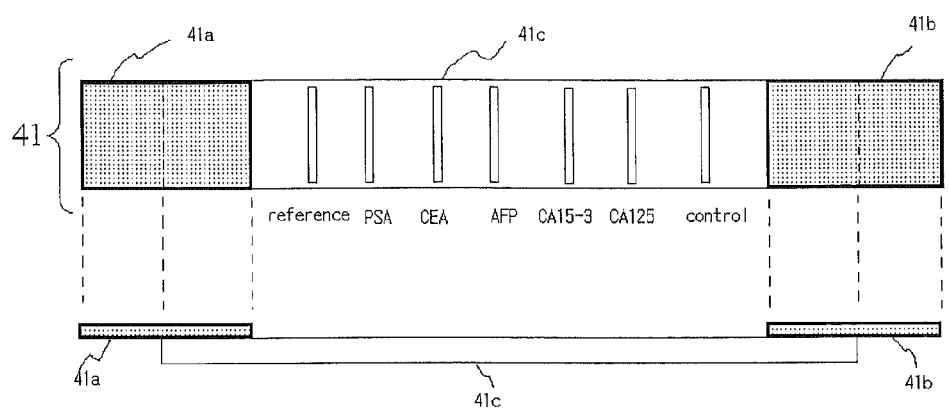

FIGS. 13 to 15 illustrate strips wherein various species of tumor markers are fixed in the form of a line or spot on the porous membrane according to one embodiment. Hereinafter, each of various species of tumor marker lines or spots is referred to as a test line.

Reference numeral 41a is a conjugate pad, a sample pad, or a combination thereof and reference numeral 41b is an absorbent pad. Reference numeral 41c is a porous membrane. A gold conjugate, an enzyme linked antibody or a label such as a fluorescent marker may be deposited in a lyophilized form on the conjugate pad. The capture probe (for example, capture antibody) can fix the tumor markers. The tumor markers may be selected from the group consisting of AFP, PSA, CEA, CA19-9, CA125 and A15-3. The capture antibody can fix glutamine synthetase (GS), a specific marker for Alzheimer's. The capture can fix myocardial infarction antibody markers such as myoglobin, CK-MB and Troponin I (TnI).

In one embodiment, the test line wherein one or more markers or capture probes for AIDS, myocardial infarction, residual antibiotics, residual pesticides, allergy and breast cancer tests are fixed on the porous membrane 41c may be applied to response tests using immunochromatography. Immunochromatography is a test method wherein immunochemistry is combined with chromatographic assay, which utilizes specific immune-response of antibody to antigens, color rendering and flowability of colloidal gold particles, and transfer of molecules on the porous membrane by capillary phenomenon. Immunochromatography is a convenient and rapid one-step method to perform processes including sample dilution, cleaning and color-rendering (chromogenesis) based on reaction of enzyme-complex with a substrate involved in conventional multi-step immunoanalysis methods. In addition, this method can easily detect test results without using any specific apparatus, thus having advantages of ease, high economic efficiency and rapid detection of test results. The capture antibody can fix, in addition to tumor markers, antibodies for reference and control lines. Plural reference lines may be present. The reaction concentration of the reference line may be a cutoff value to enable easy detection of negative or positive responses. For example, the cutoff value of the reference line may be selected from 3 ng/ml, 4 ng/ml, 10 ng/ml, 20 ng/ml, 30 ng/ml, 40 ng/ml and 50 ng/ml.

In one embodiment, the test line comprises qualitative or quantitative analysis based on the difference in reaction intensity between the reference line and the test line.

In one embodiment, the test line comprises qualitative or quantitative analysis based on the difference in reaction intensity between the background and the test line.

In one embodiment, the test line comprises qualitative or quantitative analysis performed by determining reaction intensity of the test line through a linear function of reaction intensity formed by a plurality of reference lines.

In one embodiment, the test line comprises qualitative or quantitative analysis performed by determining reaction intensity of the test line through a linear function of reaction intensity formed by the reference line and the control line.

In one embodiment, antibodies to capture free PSA are immobilized on the reference line and antibodies to capture total PSA are immobilized on the test line, to calculate percent free PSA (fPSA %). fPSA(%) can be calculated as a ratio of total PSA to free PSA. Details of the total PSA and free PSA are known in the art. In addition, free PSA may be immobilized on the test line and the total PSA may be immobilized on the reference line. In another embodiment, antibodies to capture free PSA are immobilized on the reference line and antibodies to capture proPSA are immobilized on the test line, to calculate percent proPSA (% proPSA). The proPSA (%) can be obtained by a ratio of free PSA to proPSA. Details of the proPSA are known in the art. Alternatively, proPSA may be immobilized on the reference line and the free PSA may be immobilized on the test line. Also, % fPSA and % proPSA can be simultaneously calculated by immobilizing free PSA, proPSA and total PSA on one porous membrane.

In one embodiment, the reaction intensity can be obtained from image information represented by color intensity thereof under illumination using various wavelengths of LEDs. The reaction results of the assay site 132 can be quantitatively or qualitatively analyzed based on the quadratic relationship between the various wavelengths and color intensities. The reference line shows a positive response when the specimen is diffused into the absorption pad 41b and may be used for validity of tests using strips. The test results are considered efficient, when the reference line is positive. The porous membrane 41c may be used in a flow through or lateral flow manner, which is known in the art. A specimen or a cleaning solution may be injected into the sample pad 41a. The flow through-type porous membrane may utilize strips wherein various tumor markers, disease markers or antibodies are immobilized on the porous membrane 41c. When the specimen is injected into the sample pad 41a, the specimen absorbed by the sample pad 41a is diffused throughout the porous membrane 41c by the capillary phenomenon and is thus biochemically specifically bonded to the capture antibody. The absorption pad 41b for promoting diffusion may be arranged on the terminal of the porous membrane 41c. Also, a conjugate pad may be connected to the sample pad. In this case, the liquid specimen injected into the sample pad is linked to a gold conjugate, an enzyme-linked antibody or a fluorescent material on the conjugate pad and a complex thus obtained is diffused into the porous membrane 41c. When a cleaning solution is injected into the sample pad 41a, the cleaning solution absorbed on the sample pad 41a is diffused into the porous membrane 41c by capillary action to clean materials not bound to the capture antibody or non-specifically bound thereto and thereby remove background noise from the porous membrane 41c.

In one embodiment, the assay site 132 may be set by connecting the strip 41 to the terminal of the liquid valve 7 and a portion of the sample pad 41a.

In one embodiment, the detection of the assay site 132 using the image sensor 144 comprises treating the upper base material 1 with a non-transparent material or coating the same with a non-transparent paint to prevent light scattering by illumination and noise caused by damage to substrates. In this case, for example, the transparency of the upper base material may be 20 to 50%.

Figure 16:
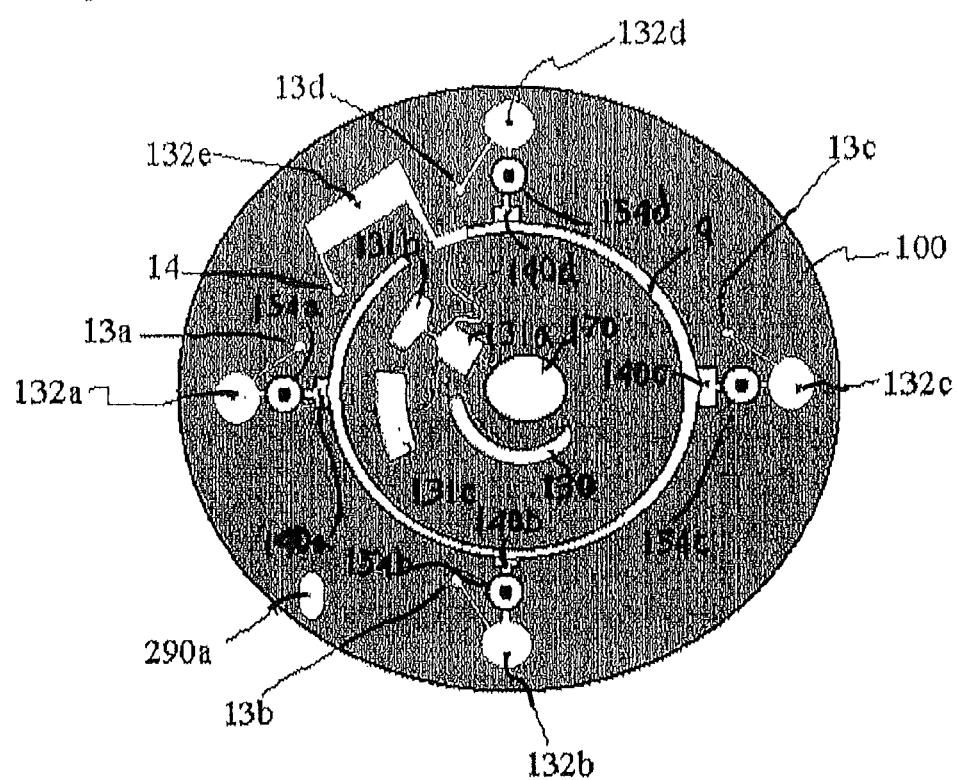
FIG. 16 illustrates a thin film centrifuge device wherein a plurality of assay sites are arranged in parallel on different sectors to perform a lab-on-a-chip process to assay various specimens with respect to a single sample according to one embodiment of the present invention.

FIG. 16 illustrates a thin film centrifuge device wherein a plurality of assay sites 132 are arranged in parallel on different sectors to perform assay of various specimens with respect to a single sample, for example, processes required for a lab-on-a-chip to assay biochemical reactions according to one embodiment of the present invention.

The term "biochemical reaction assay" used herein includes for example, assay of GOT, GPT, ALP, LDH, GGT, CPK, amylase, T-protein, albumin, glucose, T-cholesterol, triglycerides, T-bilirubin, D-bilirubin, BUN, creatinine, I. phosphorus, calcium, and uric acid in blood.

Reference numerals 132a, 132b, 132c and 132d are assay sites acting as chambers for the biochemical reaction, which store specimens to analyze and diagnose the biochemical reaction and results thereof and to perform biochemical reactions with blood serum supplied from the specimen chamber 131a. Reference numeral 7 indicates a liquid valve to prevent leakage of liquids during centrifugation of blood.

Reference numeral 290a indicates a base hole, and reference numeral 131c indicates an excess chamber. Reference numerals 154a, 154b, 154c and 154d indicate thin film valves. Reference numerals 13a, 13b, 13c, 13d and 14 indicate outlets.

During rotation of the body 100, blood stored in the sample chamber 130 is centrifuged. As a result, blood serum is stored in the specimen chamber 131a and erythrocyte is stored in the remnant chamber 131b. Set-amount chambers 140a, 140b, 140c and 140d are chambers to supply a predetermined amount of specimens to the corresponding assay sites 132a, 132b, 132c and 132d, and the volume of the set-amount chambers determines an amount of specimens supplied to the corresponding assay site. The liquid valve 7 and a concentric channel 9 are coated with a super-hydrophilic material and an overflow chamber 132e is coated with a hydrophobic material. Accordingly, when the body 100 does not rotate, the blood serum in the specimen chamber 131a hydrophilically flows through the liquid valve 7 through the concentric channel 9. The set-amount chambers 140a, 140b, 140c and 140d are chambers coated with a super-hydrophilic material, which are filled with blood serum, while specimens are passed through the concentric channel 9. In this case, the overflow chamber 132e is hydrophobic and thus only the concentric channel 9 and the set-amount chambers 140a, 140b, 140c and 140d are filled with the specimens. The concentric channel 9 is designed such that it has a concentric circle and thus receives homogeneous centrifugal force during rotation. Accordingly, after the concentric channel 9 is filled with the specimen and the body 100 rotates again, specimens are stored in the set-amount chambers 140a, 140b, 140c and 140d and remain therein, and the specimens filling the concentric channel 9 are discharged through the overflow chamber 132e by centrifugal force. Then, the thin film valves 154a, 154b, 154c and 154d open to allow specimens to flow from the set-amount chambers 140a, 140b, 140c and 40d to the respective assay sites 132a, 132b, 132c and 132d and thus induce biochemical reactions of the specimens with reagents. In one embodiment, the thin film valves 154a, 154b, 154c and 154d are concentrically arranged and thus simultaneously open. Then, biochemical reaction results of the specimens can be qualitatively or quantitatively analyzed by measuring light absorption of specimens in the assay sites 132a, 132b, 132c and 132d using the spectrometer.

In one embodiment, when the concentric channel 9 is designed such that it has a concentric circle and thus receive identical centrifugal force to rotate the thin film centrifuge device 100, only specimens present in the set-amount chambers 140a, 140b, 140c and 140d are stored and remain therein, but the specimens filling the concentric channel 9 overcome the hydrophobic barrier formed in the overflow chamber 132e by centrifugal force and are discharged to the overflow chamber 132e.

In one embodiment, the thin film valves 154a, 154b, 154c and 154d, for example, include valves such as burst valves formed in a thin-film shape to open/close openings using open/close means of thin film valves, such as valve open/close using micro-beads (or thin-film cylindrical (circular) magnets) provided in a hole with a movable permanent magnet or electric magnet arranged in an upper or lower part of the body; valve open/close by mechanical force; valve open/close by centrifugal force; valve open/close by dissolution and solidification based on chemical actions; open/close by shape memory alloys restored to original shape by heat or chemicals; valve open/close using air drops generated by electrolysis; valve open/close using air drops generated by heat; valve open/close by thermal expansion and contraction of micro-beads; valve open/close by electrostatic force; valve open/close by magnetic force; valve open/close by laser heat; valve open/close using a temperature gradient; valve open/close of an actuator based on ultrasonic waves; valve open/close based on a pump or physical pressure; valve open/close by micro particles expanded or contracted by super-high frequency; capillary burst valves; hydrophobic burst valves; valve open/close by magnetic fluid; and valve open/close by thermal expansion and contraction of air.

The hydrophobic burst valve uses a fluid flow barrier formed on the interface between the hydrophilic channel and the hydrophobic chamber, and includes hydrophobic burst valves wherein fluids cannot flow under centrifugal force of a cutoff value or less, but fluids overcome a fluid flow barrier under centrifugal force of a cutoff value or higher and move to the hydrophobic chamber. The fluid flow barrier is formed due to the facts that hydrophilic fluids cannot readily pass through a hydrophobic chamber and that the hydrophilic channel traps fluids based on inherent capillary action of the fluids.

The assay sites 132a, 132b, 132c and 132d are hydrophobic chambers and the thin film valves 154a, 154b, 154c and 154d use the hydrophobic burst valve. In this case, the set-amount chambers 140a, 140b, 140c and 140d are chambers coated with a super-hydrophilic material, and can form a fluid flow barrier at the interface with the assay site. Thin film valves including the burst valve are known in the art.

In another embodiment, a thin film valve may be further provided between an inward channel 7a of the liquid valve 7 and an outlet of the specimen chamber 131a shown in FIG. 2. In this case, when the thin film valve closes even upon non-rotation of the body 100, fluids in the specimen chamber 131a do not flow to the assay site 132, and after the thin film valve opens, fluids hydrophilic-flow through the liquid valve 7 to the assay site 132.

In one embodiment, azimuthal assay site search for measuring the spectrometer 108 can be carried out by controlling the rotation angle of the thin film centrifuge device using the stepper motors or gears connected thereto.

In one embodiment, azimuthal assay site search for measurement via the spectrometer 108 can be carried out through the azimuthal valve search process performed by arranging the thin film cylindrical magnet for searching assay sites on the circumference of the body, or by space-addressing assay sites using a blank solution chamber during rotation of the body 100 to sequentially measure light absorption in the respective assay sites during rotation of the body. In this case, the body further includes a black solution chamber having a diameter equivalent to the assay site to store the blank solution. The light absorbance of specimens in the respective assay sites is measured, after the spectrometer is calibrated such that light transmission of the blank solution is 100% (light absorbance: 0). The light absorbance of the blank solution is always zero, thus enabling sensing of the blank solution chamber during rotation of the body and thus realizing space-addressing of the assay sites based on the blank solution chamber.

The embodiments may also be applied to thin film centrifuge devices for processes associated with a lab-on-a-chip to perform enzyme-linked immunosorbent assays (ELISAs) or chemical luminescence immunosorbent assays (CLISAs). Various embodiments thereof are known in the art.

The embodiments may be also applied to thin film centrifuge devices for processes associated with a lab-on-a-chip for residual pesticide assays and residual antibiotic assays. In this case, test results derived from detection results are displayed on a computer monitor, history is reported to the servers of the corresponding government offices or food enterprises through automatic or manual remote-access thereto using an internet protocol based network, or test results and histories are stored in a memory of wireless RF ICs (electric tags). The corresponding government office can detect residual pesticide and the food enterprises can obtain purchase information of fresh crops and livestock products. In addition, the corresponding government office links this information on a web, to provide information for purchasing fresh crops and livestock products for consumers by direct transaction. Enzymes and markers for assaying residual pesticides contain enzymes and markers for assaying pesticides contained in enzymes, vegetables or fruits, for example, the most-generally used organophosphorus and carbamate insecticides. The enzyme may include acetylcholinesterase (AChE). Various embodiments thereof are known in the art.

Figure 17:
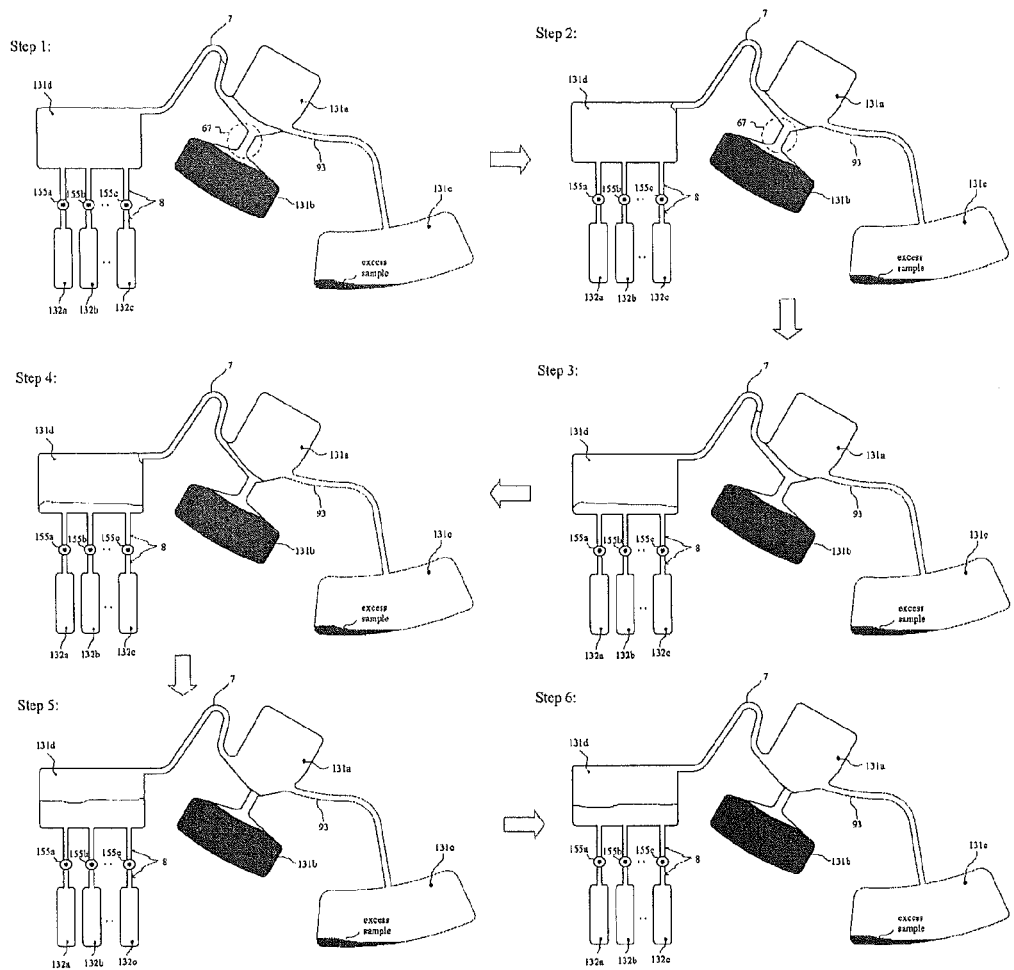
FIG. 17 illustrates a stepwise process for transferring blood serum from the specimen chamber to the buffer chamber by alternately repeating the hydrophilic fluid flow process using the liquid valve and the fluid flow process by centrifugal force.

FIG. 17 illustrates an assay site 132 different from that of FIG. 2 as another embodiment of the thin film centrifuge device 100.

In this case, the thin film centrifuge device further comprises a plurality of assay sites 132a, 132b and 132c to provide biochemical reaction assay or immunological analysis using the strip 41; a liquid valve 7 to temporarily store the specimens of the specimen chamber 131a to retain blood serum in the specimen chamber 131a during rotation of the body, when the body does not rotate, and to provide a hydrophilic fluid flow passage to transfer blood serum from the specimen chamber 131a to the buffer chamber 131d; thin film valves 155a, 155b and 155c to independently supply blood serum in the transferred buffer chamber 131d to a plurality of assay sites; and a hydrophilic channel 8 to transfer blood serum through hydrophilic fluid flows from the buffer chamber 131d to the corresponding assay site, when the thin film valves 155a, 155b and 155c open. Based on these elements, the thin film centrifuge device enables multiplex assay of a single sample. In this case, transfer of blood serum from the specimen chamber 131a to the buffer chamber 131d is carried out by alternately repeating a hydrophilic fluid flow process through the liquid valve 7 and a fluid flow process by centrifugal force.

FIG. 17 illustrates a stepwise process for transferring blood serum from the specimen chamber 131a to the buffer chamber 131d by alternately repeating the hydrophilic fluid flow process using the liquid valve 7 and the fluid flow process by centrifugal force.

In step 1, during rotation of the body after centrifugation, blood serum is collected in the specimen chamber 131a and erythrocyte is collected in the remnant chamber 131b.

In step 2, when the body does not rotate after centrifugation, blood serum of the specimen chamber 131a is charged, through the liquid valve 7, into the inward channel 7a and the outward channel 7b and hydrophilic-flows to the buffer chamber 131d.

In step 3, blood serum in the outward channel 7b flows in the buffer chamber 131d based on centrifugal force caused by rotation of the body.

In step 4, when the body ceases rotation, blood serum from the specimen chamber 131a is charged in the inward channel 7a and the outward channel 7b again through the liquid valve 7 and then hydrophilic-flows in the buffer chamber 131d.

In step 5, by repetition of steps 3 and 4, the total blood serum gradually flows from the specimen chamber 131a to the buffer chamber 131d.

In step 6, when the thin film valve 155a opens, blood serum flows through the hydrophilic channel 8 from the buffer chamber 131d to the corresponding assay site 132a. The buffer chamber 131d of FIG. 17 may be coated with a super-hydrophilic material. In this case, blood serum can readily flow from the specimen chamber to the buffer chamber by operation of the absorption pump.

Figure 18:
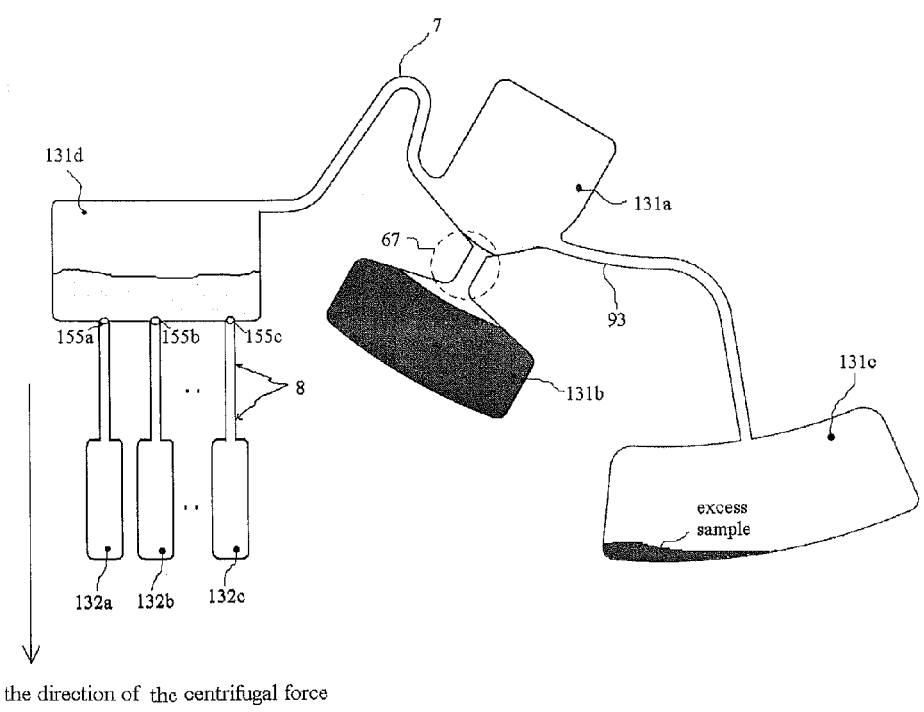
FIG. 18 illustrates a state in which blood serum flows to the assay site by centrifugal force as another embodiment different from FIG. 17.

FIG. 18 illustrates a state in which blood serum flows to the assay site by centrifugal force as another embodiment different from FIG. 17. In this case, the thin film valves 155a, 155b and 155c may be a hydrophobic burst valve or a capillary tube burst valve.

The thin film valves 155a, 155b and 155c are hydrophobic burst valves or capillary tube burst valves formed by a fluid flow barrier formed on the interface between the hydrophilic channel 8 coated with a hydrophilic material, and the hydrophobic chamber, the assay site 132a, 132b or 132c. Such a fluid flow barrier allows blood serum to not flow at a centrifugal force less than a predetermined cutoff value and allows blood serum to overcome the fluid flow barrier and then flow to the assay site 132a, 132b or 132c at a centrifugal force of the predetermined cutoff value or higher. In this case, the centrifugal force of step 3 may be applied in a level lower than the centrifugal force to overcome the fluid flow barrier.

FIGS. 19 to 22 illustrate stepwise processes of the thin film centrifuge device further comprising a dilute solution storage chamber, as compared to the embodiment shown in FIG. 17. Reference numeral 131e indicates a dilute solution storage chamber to store a dilute solution.

Figure 19:
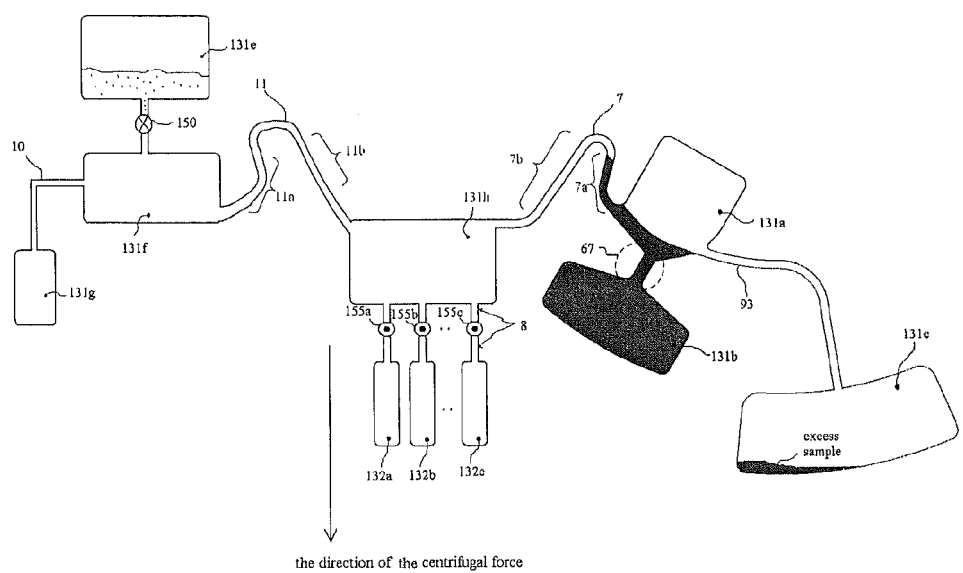
FIGS. 19 to 22 illustrate stepwise processes of the thin film centrifuge device further comprising a dilute solution storage chamber, as compared to the embodiment shown in FIG. 17.
Figure 20:
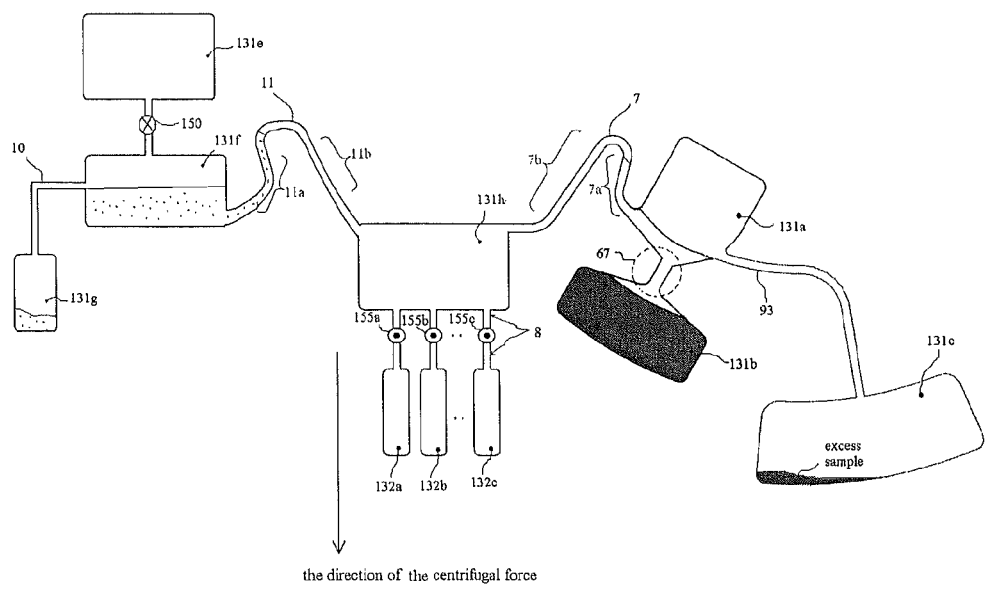

FIGS. 19 and 20 illustrate a phenomenon in which the dilute solution stored in a dilute solution storage chamber 131e flows to a buffer chamber 131f upon opening of the burst valve 150, while specimens in the specimen chamber 131a are centrifuged. In this case, the dilute solution stored in the buffer chamber 131*f* is retained by the liquid valve 11. Similarly, specimens in the specimen chamber 131*a* are also retained in the specimen chamber 131*a* through the liquid valve 7 during centrifugation. Excess dilute solution in the buffer chamber 131*f* flows through a set-amount channel 10 to an excess chamber 131*g* to allow a desired amount of the dilute solution to be stored in the buffer chamber 131*f*.

Figure 21:
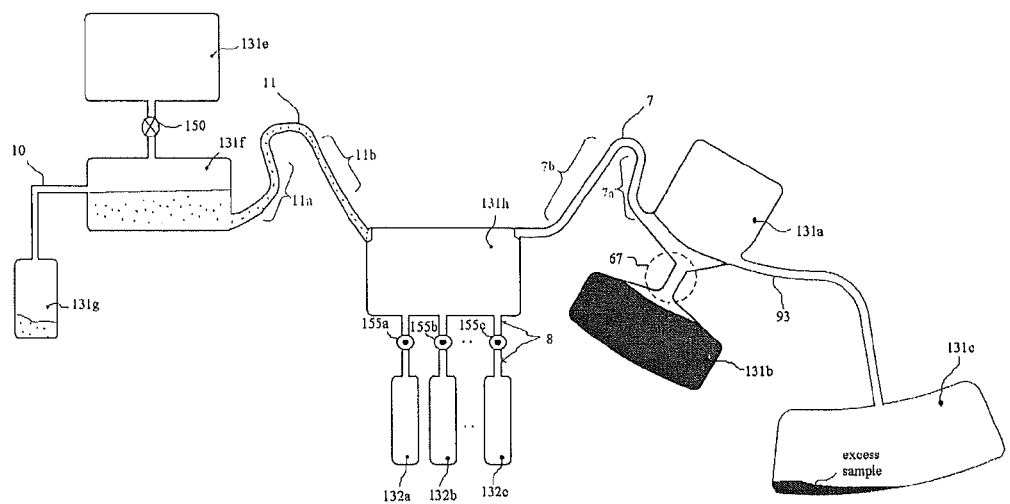

FIG. 21 illustrates a process in which blood serum in the specimen chamber 131*a* is charged in the inward channel 7*a* and the outward channel 7*b* through the liquid valve 7, when the body ceases rotation, and hydrophilic-flows to a mixing chamber 131*h*. In addition, FIG. 21 illustrates a process in which the dilute solution in the buffer chamber 131*f* is charged in an inward channel 11*a* and an outward channel 11*b* through the liquid valve 11 and then hydrophilic-flows to the mixing chamber 131*h*.

Figure 22:
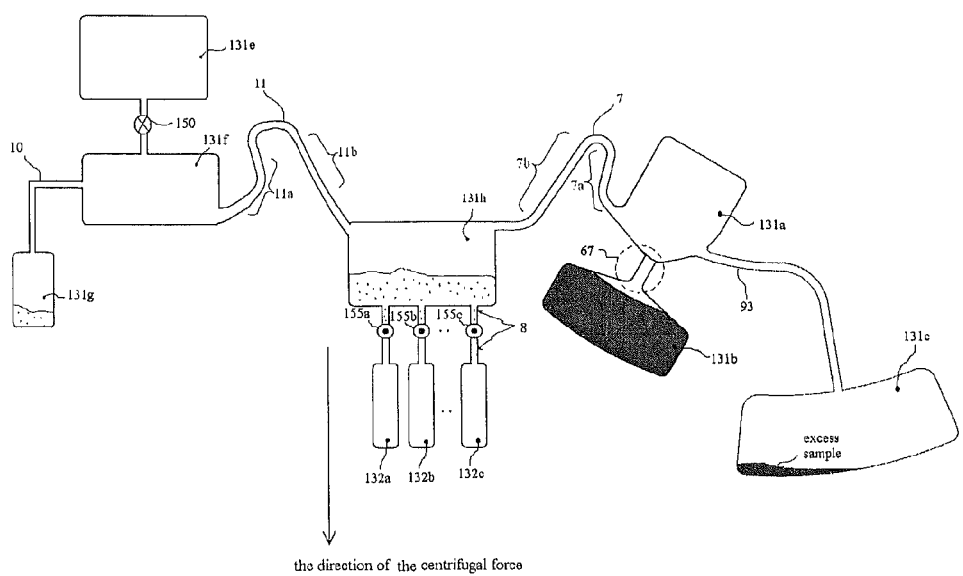

FIG. 22 illustrates a phenomenon wherein the specimen and the dilute solution are gradually transferred to the mixing chamber 131*h* through repetition of a process for transferring fluids in the outward channels 7*b* and 11*b* to the mixing chamber 131*h* based on centrifugal force caused by rotation of the body and a process for filling the inward channels 7*a* and 11*a* and the outward channels 7*b* and 11*b* with hydrophilic fluids, after ceasing rotation of the body. Accordingly, the dilute solution is mixed with the specimens in the mixing chamber 131*h* to produce a diluted specimen.

In the process for gradually transferring the specimen and the dilute solution to the mixing chamber 131*h* via repetition of the hydrophilic fluid flow through the liquid valve and fluid flow based on centrifugal force, the specimen is gradually mixed with the dilute solution to maximize mixing efficiency between these fluids. Hereinafter, the mixing of the specimen with the dilute solution is referred to as a gradual mixing during the process for gradually transferring the specimen and the dilute solution to the mixing chamber 131*h*.

Closing strength of the hydraulic burst valve is determined, based on an adhesion area of a thin-film adhesive tape, when holes are clogged by the thin film adhesive tape, and a valve to allow the thin film adhesive tape to be detached at a disc rotational speed (centrifugal force) or higher to overcome the closing strength and thereby open the hole.

The burst valve may be, for example, a hydraulic burst valve, which is known in the art.

Figure 23:
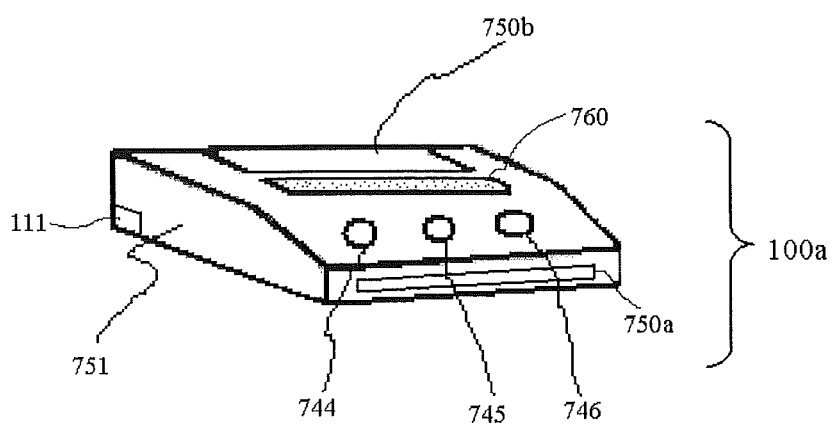
FIG. 23 illustrates a thin film layered centrifuge device drive to front-load or top-load the thin film centrifuge device according to one embodiment of the present invention.

FIG. 23 illustrates a thin film layered centrifuge device drive 100*a* to front-load or top-load the thin film centrifuge device according to one embodiment of the present invention. The thin film centrifuge device 100 may be loaded on the thin film layered centrifuge device drive 100*a*. Reference numeral 751 indicates a case of the thin film layered centrifuge device drive and reference numeral 750*a* indicates a tray to front-load the thin film centrifuge device 100. In addition, reference numeral 750*b* indicates a cover to perform top-loading. When the cover opens, the hole 170 of the thin film centrifuge device may be mounted on the turn table. Based on a loading type, one may be selected from reference numeral 750*a* and reference numeral 750*b*. In addition, according to one embodiment of the present invention, the thin film layered centrifuge device drive may optionally comprise a reading/searching button 745 or a stop button 746 to read conventional optical discs. Reference numeral 744 indicates an on/off button of the thin film centrifuge device drive.

Reference numeral 760 indicates a display device to show a process state and mode of the thin film layered centrifuge device drive. A light-emitting diode or an LCD may be used as the display device. The display device 760 displays whether the loaded disc is a thin film centrifuge device or an optical disc, analysis results or a main process state of the thin film layered centrifuge device drive. Alternatively, the display device 760 displays a graphical user interface and a process rate in accordance with the step in the form of a percent (%), a bar graph or a pie graph.

Reference numeral 111 indicates an input/output device to realize automatic or manual remote contact with a doctor of the corresponding field through an internet network and to remote-transmit diagnosis results and questionnaires to the doctor, if necessary. Then, patients wait for a prescription from the doctor.

The thin film layered centrifuge device drive shown in FIG. 8 may further comprise a speaker, a moving-image camera and/or a microphone. In the case of non-advanced cancers, a level of tumor markers in blood does not increase, and in the case of early cancers, a level of tumor markers in blood is within a normal range and it increases and positive ratio thereof also increases, as the tumors progress. In one embodiment, taking this fact into consideration, the centrifuge device comprises statistical software to historically manage detection results derived from quantitative analysis of the assay site to provide information associated with regular trace diagnosis to a user.

In addition, in one embodiment, the thin film layered centrifuge device drive may further comprise software to read and analyze the response results and to analyze negative or positive response, presence of risk groups or values.

Also, in one embodiment, the thin film layered centrifuge device drive allows side loading or vertical loading of the thin film centrifuge device.

As apparent from the afore-going, the thin film layered centrifuge device and an analysis method using the same according to one embodiment may be applied to thin-film devices to diagnose and detect a small amount of biological and/or chemical materials in fluids, such as a lab-on-a-chip, protein chips and DNA chips. For example, the thin film centrifuge device may be applied to integrate centrifuge devices in thin film discs such as conventional CD-ROMs or DVDs.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A centrifuge device comprising:
 a sample inlet to inject a sample;
 a sample chamber to store the sample injected into the sample inlet;
 a specimen chamber to store a specimen obtained from the sample during centrifugation;
 a remnant chamber to store a remnant rather than specimens produced during centrifugation;
 a bottle neck channel to connect the specimen chamber to the remnant chamber;
 one or more assay sites in which a capture probe to be bound to the specimen is immobilized and/or reagent for biochemical reactions with the specimen is stored;
 a trash chamber to collect debris not bound to the capture probe by a washing process;
 a rotatable hydrophobic body in which the sample inlet, the sample chamber, the specimen chamber, the remnant chamber, the trash chamber, the bottle neck channel and the assay site are integrated;
 one or more fluid flow devices to transfer the specimen from the specimen chamber to the assay site upon non-rotation of the body, the fluid flow devices selected from the group consisting of a hydrophilic fluid flow pump, a chamber pump and an erythrocyte pump and an absorption pump; and a liquid valve, to provide a passage to connect the specimen chamber to the assay sites, allowing the specimen retained in the specimen chamber during centrifugation to flow to the assay site by the fluid flow device upon non-rotation of the body, wherein an absorbent pad or a sample pad is provided between the terminal of the liquid valve and an inlet of the assay site, to transfer the specimen from the specimen chamber to the assay site, based on an absorption force to absorb the specimen reaching the terminal of the liquid valve.

2. The device according to claim 1, wherein the liquid valve comprises an inward channel and an outward channel to form a U- or V-shape.

3. The device according to claim 1, further comprising a thin film valve provided between the liquid valve and the outlet of the specimen chamber.

4. The device according to claim 1, further comprising a set-amount channel and an excess chamber to store excess specimen or sample present in the specimen chamber.

5. The device according to claim 1, wherein the remnant chamber is a capillary tube chamber.

6. The device according to claim 1, wherein the body comprises one or more chambers selected from the group consisting of cleaning chambers, mixing chambers, buffer chambers and substrate chambers.

7. The device according to claim 6, further comprising:
magnetic micro-beads contained in the mixing chamber;
a slider movable in a lower part of the body; and
a permanent magnet mounted on the slider, to apply attraction force to the magnetic micro-beads and thus move the magnetic micro-beads,
wherein the magnetic micro-beads are moved in accordance with movement of the slider to induce mixing of liquids in the mixing chamber.

8. The device according to claim 6, further comprising:
magnetic micro-beads contained in the mixing chamber;
a slider movable in a lower part of the body; and
a permanent magnet mounted on the slider, to attract the magnetic micro-beads and thus move the magnetic micro-beads,
wherein the permanent magnet is maintained on the corresponding diameter in the mixing chamber and the body is rotated to induce movement of the magnetic micro-beads, thereby mixing of the liquids in the mixing chamber.

9. The device according to claim 1, wherein the bottle neck channel comprises two or more thin film channels.

10. The device according to claim 9, wherein the thin film channels are formed between base material layers to constitute the body by a channel-shaped thin film adhesive tape.

11. The device according to claim 1, wherein the body comprises an upper base material, an intermediate base material and a lower base material which are laminated in this order and adhered to one another,
wherein the body further comprises:
a first thin film adhesive tape laminated between the upper base material and the intermediate base material, to adhere the upper base material to the intermediate base material; and a second thin film adhesive tape laminated between the intermediate base material and the lower base material, to adhere the intermediate base material to the lower base material.

12. The device according to claim 11, wherein the substrate is composed of at least one selected from the group consisting of hydrophobic materials, silicon wafers, polypropylene, polyacylate, polyvinylalcohol, polyethylene, polymethyl methacrylate (PMMA), cyclic olefin copolymers (COCs) and polycarbonate.

13. The device according to claim 1, wherein the assay site comprises a porous membrane or a strip in which the capture probe is fixed.

14. The device according to claim 1, wherein the body comprises a wireless RF IC having one or more functions selected from the group consisting of temperature measurement, assay site detection, storage and transmission of assay site detection results, personal privacy encryption, identification (ID) storage and transmission of the thin film centrifuge device, test date storage and efficient period storage.

15. The device according to claim 14, further comprising a wireless electric wave generator to supply power to the wireless RF IC.

16. The device according to claim 15, wherein the wireless electric wave generator comprises a multipole permanent magnet to generate an electric current in an induction coil provided in the wireless RF IC by an alternating magnetic field generated by rotation of the body.

17. The device according to claim 1, wherein the body further comprises:
a preparation chamber to prepare DNA or RNA from blood serum obtained from the specimen chamber;
an amplification chamber to amplify the DNA and RNA; and
a fragmentation chamber to fragment the amplified DNA to a predetermined length.

18. The device according to claim 17, wherein the body further comprises a thin film cylindrical magnet or thin film ferromagnetic metal particles to space-address the preparation chamber, the amplification chamber, the fragmentation chamber, the assay site or the mixing chamber.

19. The device according to claim 18, further comprising one or more selected from the group consisting of temperature measurement devices, heating devices and cooling devices to control temperatures of the chambers.

20. The device according to claim 1, further comprising a set-amount chamber coated with a super-hydrophilic material and a concentric channel coated with a super-hydrophilic material,
wherein the set-amount chamber is interposed between the concentric channel and the assay site,
wherein the concentric channel is connected to an outlet of the liquid valve,
the device further comprising an overflow chamber to allow the specimen to remain in the set-amount chamber by rotation of the body and the specimen in the concentric channel to be extracted by centrifugal force and thereby store the residual specimen, after the set-amount chamber and the concentric channel are filled with the specimen, while the specimen in the specimen chamber hydrophilic-flows through the concentric channel.

21. The device according to claim 20, wherein the specimen of the set-amount chamber overcomes the fluid flow barrier formed between the set-amount chamber and the assay site by centrifugal force generated by rotation of the body and then flows in the assay site.

22. The device according to claim 1, wherein the remnant chamber comprises neither a channel nor an outlet to allow liquids to flow in or leak out, except the bottle neck channel.

23. A thin film centrifuge device for realizing a multiplex assay with a single sample, comprising:
- a sample inlet to inject a sample;
- a sample chamber to store the sample injected into the sample inlet;
- a specimen chamber to store a specimen obtained from the sample during centrifugation;
- a remnant chamber to store a remnant rather than specimens produced during centrifugation;
- a bottle neck channel to connect the specimen chamber to the remnant chamber;
- a dilute solution storage chamber to store a dilute solution;
- a hydraulic burst valve provided in an output of the dilute solution storage chamber, the hydraulic burst valve opened by a fluid pressure generated by rotation of the body;
- a buffer chamber to temporarily store the specimen moved from the specimen chamber by alternately repeating a hydrophilic fluid flow process through the liquid valve and a fluid flow process by centrifugal force;
- a liquid valve coated with a hydrophilic material, to provide a hydrophilic fluid passage to retain the specimen in the specimen chamber during rotation of the body, and move the specimen to the specimen chamber upon non-rotation thereof;
- a mixing chamber to perform gradual mixing and temporary storage by gradually moving the specimen and the dilute solution through alternate repetition of a hydrophilic fluid flow process through the liquid valve and a fluid flow process by centrifugal force;
- one or more assay sites in which a capture probe to be bound to the specimen is immobilized and/or a reagent for biochemical reactions with the specimen is stored;
- a thin film valve to supply the specimen present in the mixing chamber to the assay sites;
- a rotatable hydrophobic body in which the sample inlet, the sample chamber, the specimen chamber, the remnant chamber, a trash chamber, the bottle neck channel and the assay site are integrated; and
- a hydrophilic channel interposed between the mixing chamber and the assay site, to hydrophilic-flow the specimen from the mixing chamber to the assay site, when the thin film valve opens.

24. The device according to claim 1, wherein the absorbent pad or the sample pad is provided between the terminal of the liquid valve and an inlet of the assay site, to transfer the specimen from the specimen chamber to the absorbent pad or the sample pad, based on an absorption force to absorb the specimen reaching the terminal of the liquid valve.

25. A thin film centrifuge device for realizing a multiplex assay with a single sample, comprising:
- a sample inlet to inject a sample;
- a sample chamber to store the sample injected into the sample inlet;
- a specimen chamber to store a specimen obtained from the sample during centrifugation;
- a remnant chamber to store a remnant rather than specimens produced during centrifugation;
- a bottle neck channel to connect the specimen chamber to the remnant chamber;
- a liquid valve coated with a hydrophilic material, to provide a hydrophilic fluid passage to retain the specimen in the specimen chamber during rotation of the body, and move the specimen to the specimen chamber upon non-rotation thereof;
- a buffer chamber to temporarily store the specimen that was previously stored in the specimen chamber by alternately repeating a hydrophilic fluid flow process through the liquid valve and a fluid flow process by centrifugal force;
- one or more assay sites in which a capture probe to be bound to the specimen is immobilized and/or a reagent for biochemical reactions with the specimen is stored;
- a thin film valve to supply the specimen present in the buffer chamber to the assay sites;
- a rotatable hydrophobic body in which the sample inlet, the sample chamber, the specimen chamber, the remnant chamber, a trash chamber, the bottle neck channel and the assay site are integrated; and
- a hydrophilic channel interposed between the buffer chamber and the assay site, to hydrophilic-flow the specimen from the buffer chamber to the assay site, when the thin film valve opens.

26. The device according to claim 25, wherein the thin film valve is a hydrophobic burst valve or a capillary tube burst valve.

27. The device according to any one of claims 1, 13, 25 and 23, wherein the assay site comprises a fixed capture probe to analyze percent free PSA (% fPSA) or percent proPSA (% proPSA).

* * * * *

UNITED STATES PATENT AND TRADEMARK OFFICE
CERTIFICATE OF CORRECTION

| | | |
|---|---|---|
| PATENT NO. | : 8,969,070 B2 | Page 1 of 1 |
| APPLICATION NO. | : 12/863684 | |
| DATED | : March 3, 2015 | |
| INVENTOR(S) | : Jae Chern Yoo | |

It is certified that error appears in the above-identified patent and that said Letters Patent is hereby corrected as shown below:

In the Claims

Claim 12, Column 30, Line 8

Delete "polyacylate," and insert --polyacrylate,--, therefor

Claim 14, Column 30, Line 20

Delete "date" and insert --data--, therefor

Signed and Sealed this
Fifteenth Day of September, 2015

Michelle K. Lee
*Director of the United States Patent and Trademark Office*